US012636391B2

(12) United States Patent
Grinstead

(10) Patent No.: US 12,636,391 B2
(45) Date of Patent: May 26, 2026

(54) FOGGING DEVICE WITH DIFFERENT OPERATIONAL MODES FOR FOGGING ACCESSORIES AND RELATED METHODS

(71) Applicant: GCMG COMPANIES, LLC, Oviedo, FL (US)

(72) Inventor: Steven T. Grinstead, Oviedo, FL (US)

(73) Assignee: GCMG COMPANIES, LLC, Oviedo, FL (US)

( * ) Notice: Subject to any disclaimer, the term of this patent is extended or adjusted under 35 U.S.C. 154(b) by 759 days.

(21) Appl. No.: 18/056,014

(22) Filed: Nov. 16, 2022

(65) Prior Publication Data
US 2023/0158191 A1     May 25, 2023

Related U.S. Application Data

(60) Provisional application No. 63/264,526, filed on Nov. 24, 2021.

(51) Int. Cl.
*A61L 2/24* (2006.01)
*A61L 2/22* (2006.01)
(Continued)

(52) U.S. Cl.
CPC ...... *A61L 2/24* (2013.01); *A61L 2/22* (2013.01); *A61L 9/14* (2013.01); *A61L 2103/75* (2026.01);
(Continued)

(58) Field of Classification Search
CPC ..... A61L 2/24; A61L 2/22; A61L 9/14; A61L 2202/14; A61L 2202/15; A61L 2202/16;
(Continued)

(56) References Cited

U.S. PATENT DOCUMENTS 9,717,810 B2 * 8/2017 Grinstead ................. A61L 2/22
10,092,668 B2 10/2018 Grinstead
(Continued)

FOREIGN PATENT DOCUMENTS

WO     WO-2018056300 A1 * 3/2018 .......... A61M 11/041
WO     WO-2019222159 A1 * 11/2019 .......... A61M 16/162

OTHER PUBLICATIONS

English translation of Nakano (WO 2018056300 A1). (Year: 2018).*
(Continued)

*Primary Examiner* — Maris R Kessel
*Assistant Examiner* — Aham Lee
(74) *Attorney, Agent, or Firm* — Allen, Dyer, Doppelt + Gilchrist, PA

(57) ABSTRACT

A fogging system may include a fogging device including a fluid reservoir, a first fluid atomizer coupled to the fluid reservoir, and a processor configured to operate the first fluid atomizer to atomize fluid from the fluid reservoir in a first operating mode. The system may further include at least one fogging accessory removably attachable to the fogging device and comprising circuitry configured to identify a fogging accessory device type associated with the at least one fogging accessory, and a second fluid atomizer configured to atomize fluid from the fluid reservoir when the at least one fogging accessory is attached to the fogging device. The processor may be configured to detect the fogging accessory device type from the circuitry and switch to a second operating mode responsive to the detection, with the second operating mode being different than the first operating mode.

20 Claims, 22 Drawing Sheets

(51) Int. Cl.
  A61L 9/14 (2006.01)
  A61L 103/75 (2026.01)

(52) U.S. Cl.
  CPC ....... *A61L 2202/14* (2013.01); *A61L 2202/15*
    (2013.01); *A61L 2202/16* (2013.01); *A61L*
    *2209/11* (2013.01); *A61L 2209/134* (2013.01)

(58) Field of Classification Search
  CPC ............. A61L 2202/25; A61L 2209/11; A61L
    2209/134; A61L 2202/24
  See application file for complete search history.

(56)                References Cited

U.S. PATENT DOCUMENTS

| | | | |
|---|---|---|---|
| 10,894,107 B2 | 1/2021 | Grinstead et al. | |
| 10,987,444 B2 | 4/2021 | Grinstead | |
| 11,291,740 B2 | 4/2022 | Grinstead et al. | |
| 2021/0128766 A1 | 5/2021 | Grinstead et al. | |
| 2021/0252179 A1 | 8/2021 | Grinstead | |
| 2021/0386889 A1* | 12/2021 | Solitro ...................... | A61L 2/10 |
| 2022/0226524 A1 | 7/2022 | Grinstead et al. | |

OTHER PUBLICATIONS

Reintech "Patent: Hydrogen Peroxide Pass Through" https://reintech.
com.br/en/news/patent-hydrogen-peroxide-pass-through; Retrieved
from internet Mar. 15, 2022; pp. 3.

* cited by examiner

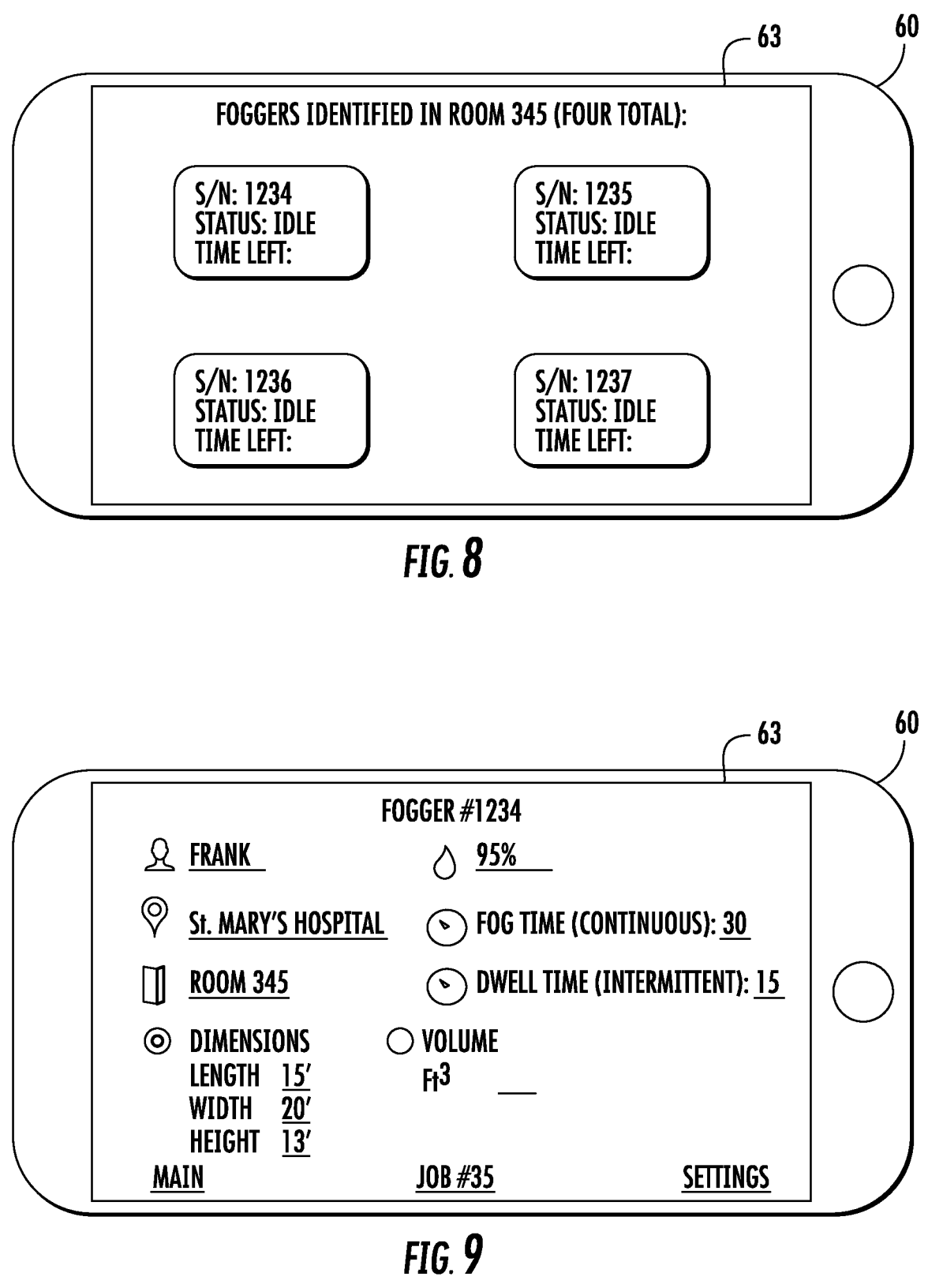

63

60

FOGGERS IDENTIFIED IN ROOM 345 (FOUR TOTAL):

S/N: 1234
STATUS: IDLE
TIME LEFT:

S/N: 1235
STATUS: IDLE
TIME LEFT:

S/N: 1236
STATUS: IDLE
TIME LEFT:

S/N: 1237
STATUS: IDLE
TIME LEFT:

FOGGER #1234

FRANK

95%

St. MARY'S HOSPITAL

FOG TIME (CONTINUOUS): 30

ROOM 345

DWELL TIME (INTERMITTENT): 15

DIMENSIONS
LENGTH  15'
WIDTH  20'
HEIGHT  13'

VOLUME
Ft$^3$  _____

MAIN        JOB #35        SETTINGS

*FIG. 9*

FOGGING DEVICE WITH DIFFERENT OPERATIONAL MODES FOR FOGGING ACCESSORIES AND RELATED METHODS

The application claims the benefit of U.S. provisional application No. 63/264,526 filed Nov. 24, 2021, which is hereby incorporated herein in its entirety by reference.

TECHNICAL FIELD

Technical Field

The present invention relates to the field of disinfecting, deodorizing, preserving, or sterilizing, and, more particularly, to apparatuses and methods for delivery of disinfecting, deodorizing, preserving, or sterilizing solutions.

Background

Disinfection and sterilization are particularly important in the field of healthcare to ensure that infectious pathogens are not transmitted to patients via medical devices or the environment in which patients are treated. While medical instruments may be placed in autoclaves or other sterilization chambers for sterilization, sterilization of the atmosphere and surfaces within a patient or operating room can be more difficult and labor intensive to perform properly. Moreover, there is evidence to show that a manual "spray and wipe", in addition to being labor and time intensive, is not always a suitably effective process for disinfection. More particularly, spray and wipe allows for human error (missing areas where pathogens reside), and may also allow for cross-contamination (spreading of germs).

While spray and wipe processes remain an important component of a disinfection strategy for certain applications, more contemporary methods such as fogging for whole room disinfection may be desirable to help ensure that all surfaces, whether visible or not, are reached for effective pathogen elimination.

SUMMARY

A fogging system may include a fogging device including a fluid reservoir, a first fluid atomizer coupled to the fluid reservoir, and a processor configured to operate the first fluid atomizer to atomize fluid from the fluid reservoir in a first operating mode. The system may further include at least one fogging accessory removably attachable to the fogging device and comprising circuitry configured to identify a fogging accessory device type associated with the at least one fogging accessory, and a second fluid atomizer configured to atomize fluid from the fluid reservoir when the at least one fogging accessory is attached to the fogging device. The processor may be configured to detect the fogging accessory device type from the circuitry and switch to a second operating mode responsive to the detection, with the second operating mode being different than the first operating mode.

In an example embodiment, the at least one fogging accessory may comprise a plurality of different fogging accessories having different respective fogging accessory device types, and the second operating mode may comprise a plurality of different accessory operating modes each for a respective fogging accessory device type. By way of example, the at least one fogging accessory may comprise a room integration fogging device. In accordance with another example, the at least one fogging accessory may comprise a hand sprayer. In still another example implementation, the at least fogging accessory may comprise a fogging injection station for an enclosed chamber.

In one example implementation, the fogging device may further include a pump coupled to the fluid reservoir, and the processor may be configured to operate the pump to prime the at least one fogging accessory in the second operating mode. In another example implementation, the processor may be further configured to operate the pump to dispense fluid from the fluid reservoir differently during the first and second operating modes.

In some embodiments, the processor may be further configured to detect a compliance mode device adjacent the fogging device, and prohibit operation of the second fluid atomizer in the second operating mode when the compliance mode device is not detected. In an example implementation, the fogging device may further include an LED indicator coupled to the processor, and the processor may be further configured to operate the LED indicator differently in the first and second operating modes. In still another example embodiment, the fogging device may further include a data port coupled to the processor, and the processor may be configured to detect the fogging accessory device type via a wired communications link between the data port and the at least one fogging accessory.

A related fogging device, such as the one discussed briefly above, and non-transitory computer-readable medium for such a fogging device are also provided. The non-transitory computer-readable medium may have computer-executable instructions for causing the processor to perform steps including operating the first fluid atomizer to atomize fluid from the fluid reservoir in a first operating mode based upon an operating parameter. For at least one fogging accessory removably attachable to the fogging device and comprising circuitry configured to identify a fogging accessory device type associated with the at least one fogging accessory and a second fluid atomizer configured to atomize fluid from the fluid reservoir when the at least one fogging accessory is attached to the fogging device, the steps may further include detecting the fogging accessory device type from the circuitry, and switching to a second operating mode responsive to the detection, with the second operating mode being different than the first operating mode.

BRIEF DESCRIPTION OF THE DRAWINGS

FIGS. 8-11 are screen shots of a mobile wireless communications device which may be used with the system of FIG. 7 illustrating various control screens for operating the fogging devices.

DETAILED DESCRIPTION

Figure 1:
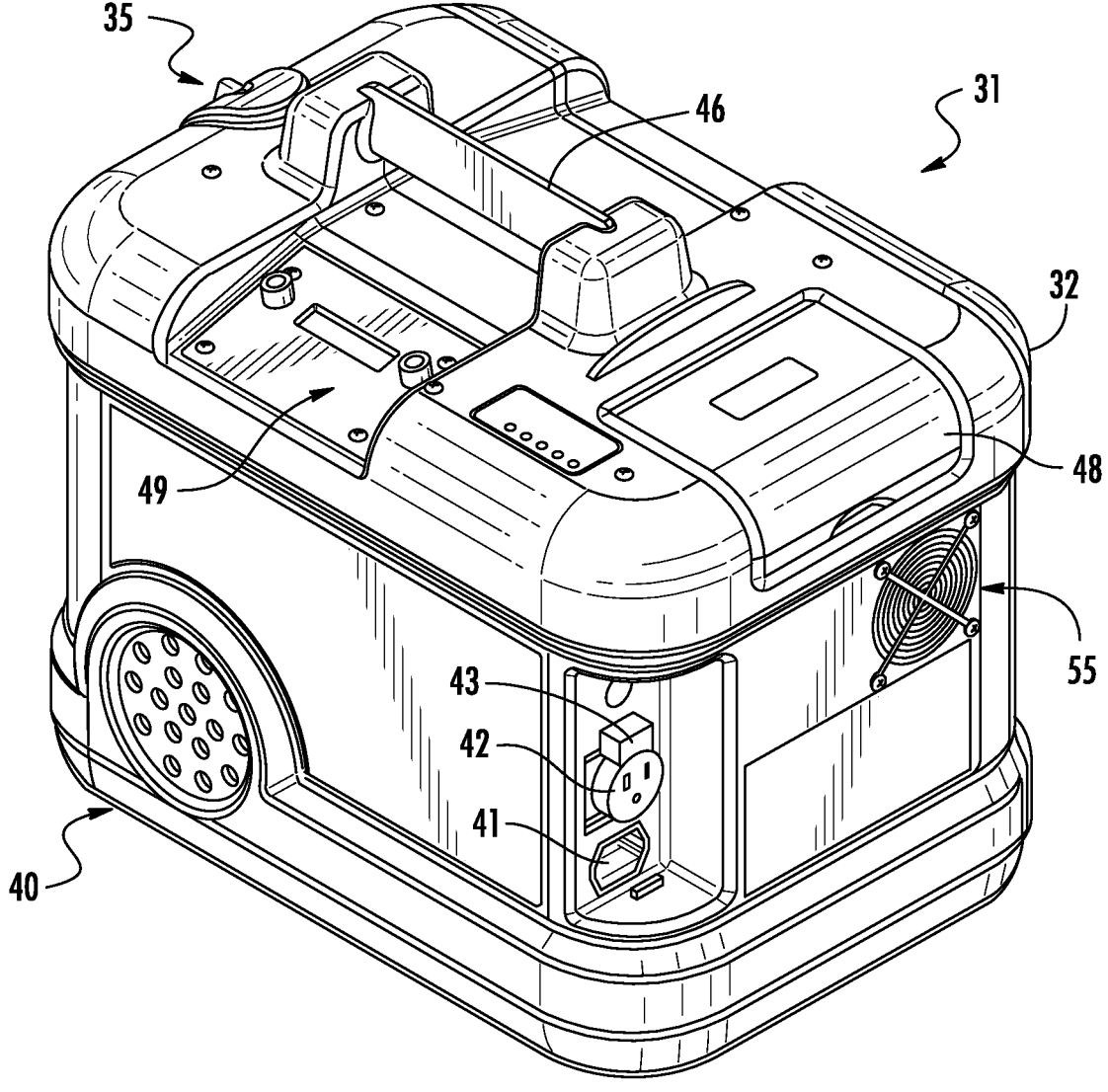
FIG. 1 is perspective view of a fogging device in accordance with an example embodiment.
Figure 2A:
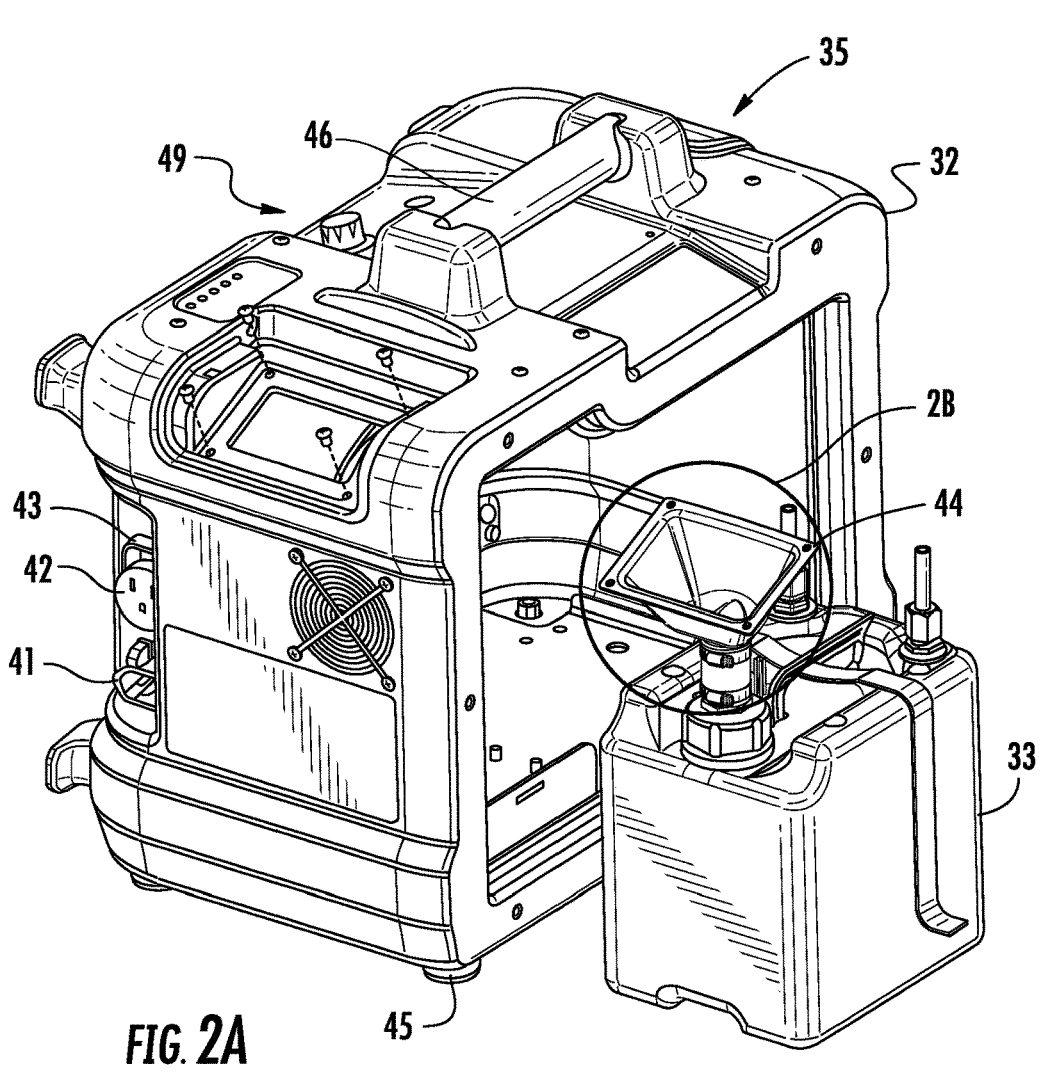
FIG. 2A is a perspective view of the fogging device of FIG. 1 with a side panel removed and illustrating installation of a fluid reservoir therein.
Figure 2B:
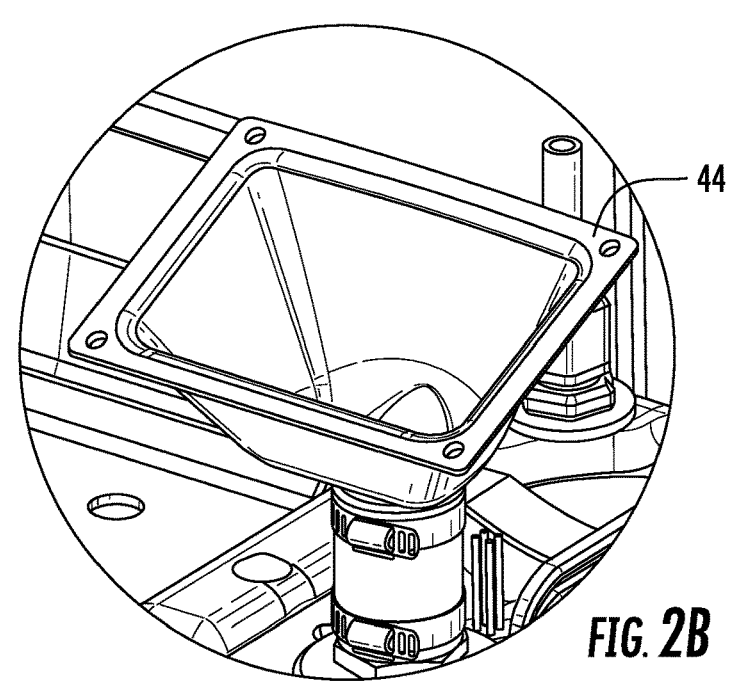
FIG. 2B is a perspective view of the area B of FIG. 2A illustrating an example funnel assembly for the fluid reservoir in greater detail.
Figure 3:
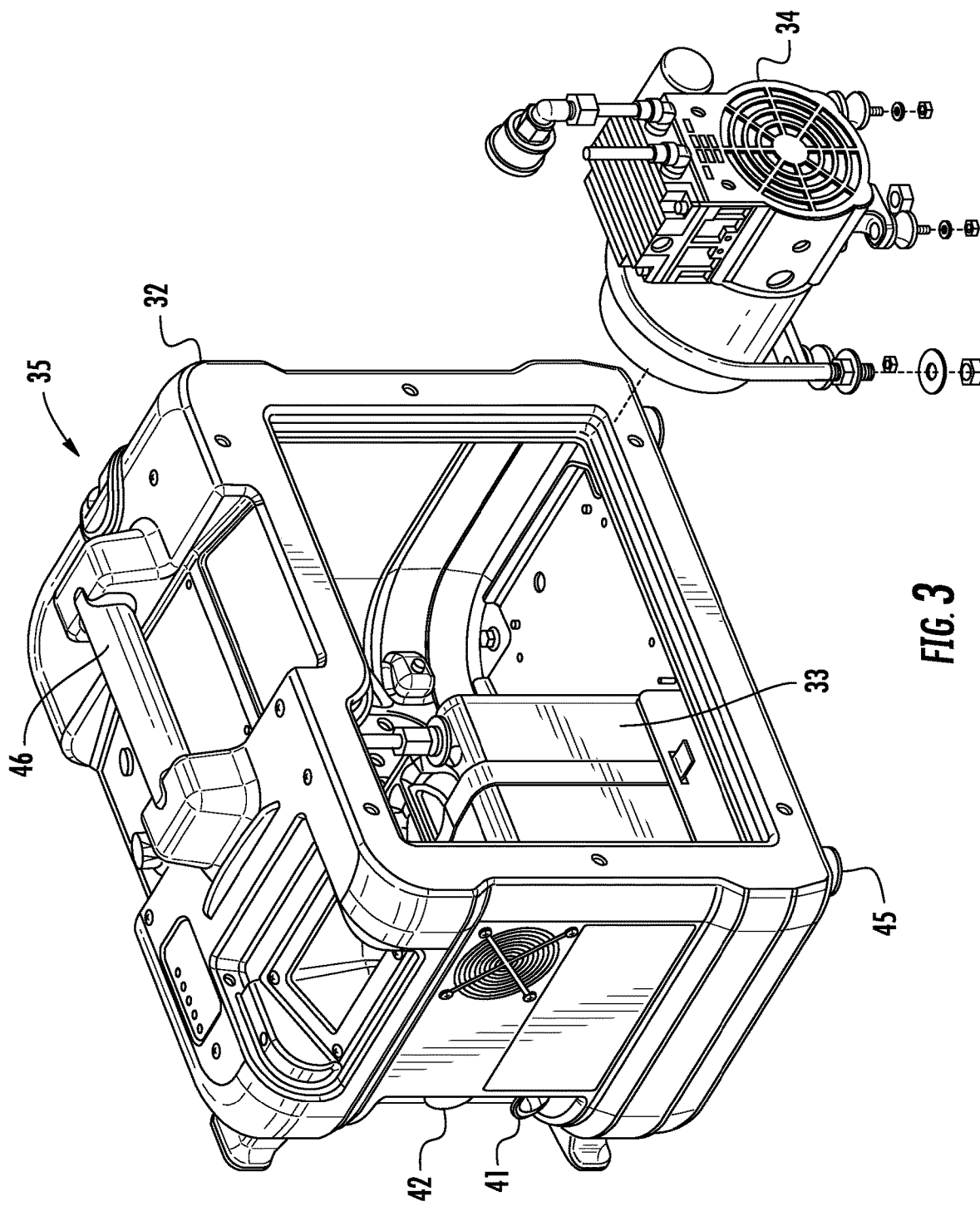
FIG. 3 is a perspective view of the fogging device of FIG. 1 with the side panel removed and illustrating installation of a compressor therein.
Figure 4:
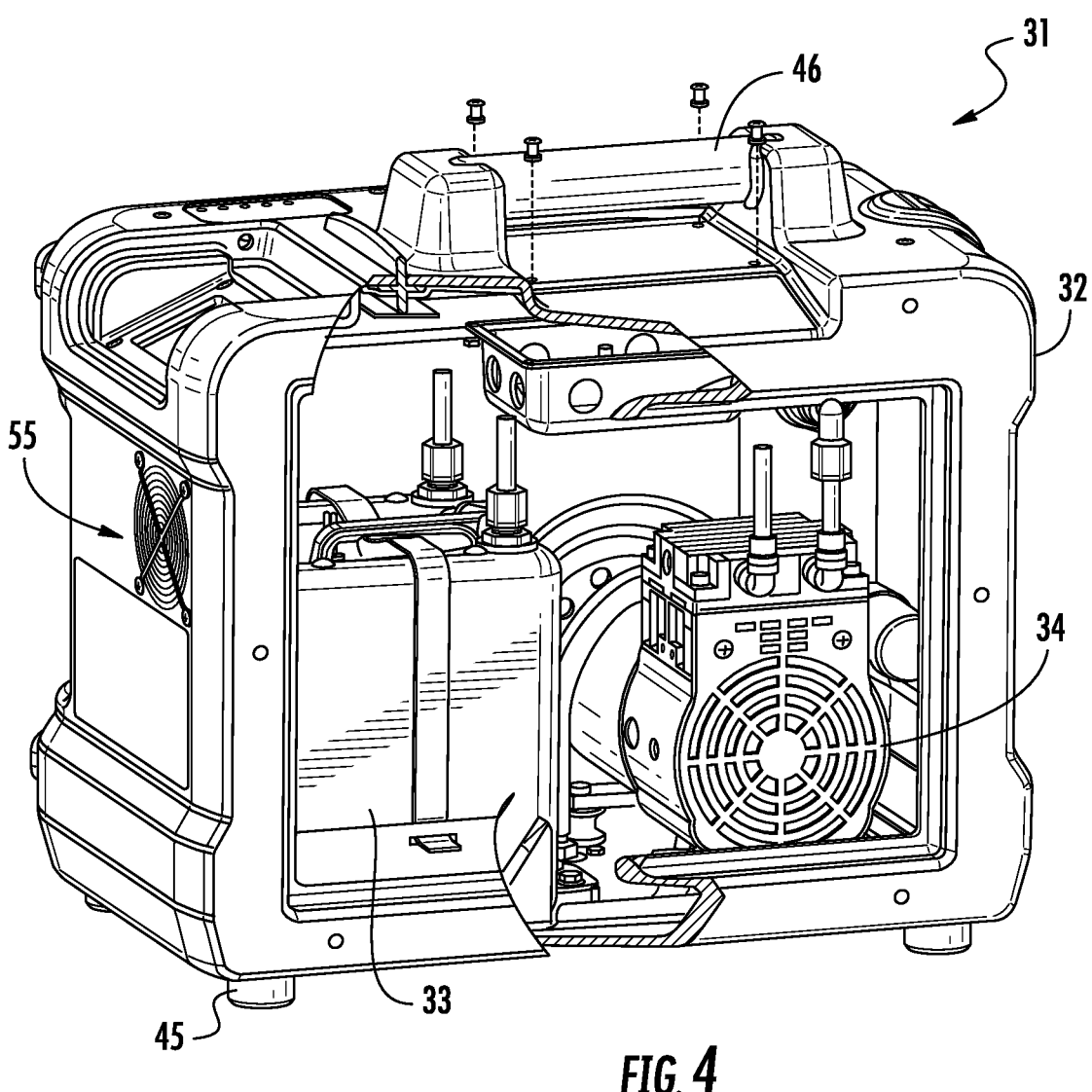
FIG. 4 is a perspective view of the fogging device of FIG. 1 with the side panel removed after installation of the fluid reservoir and compressor.

The present disclosure is provided with reference to the accompanying drawings, in which various embodiments are shown. However, other embodiments in many different forms may be used, and the disclosure should not be construed as limited to the particular embodiments set forth herein. Rather, these embodiments are provided so that this disclosure will be thorough and complete, and will fully convey the claim scope to those skilled in the art. Like numbers refer to like elements throughout.

Referring initially to FIGS. 1-7 and 14, the present disclosure relates to a fogging or atomizing system 30 which may be used for the application of a chemical solution to a treatment area for the purposes of disinfecting, deodorizing, preserving, pesticide application, or sterilizing the area or items within the area, for example. By way of example, the fogging system may be used for application of a disinfectant chemical to an enclosed area, including one or more rooms in a building, as well as in vehicles such as buses, ships/boats, airplanes, subway or train cars, automobiles, trucks, etc. In the example illustrated in FIG. 7, those components schematically shown on the right of the vertical dashed line are considered to be within the enclosed treatment area.

The fogging system 30 illustratively includes a plurality of fogging devices or foggers 31 which are to be positioned within the enclosed treatment area (FIG. 7) to perform a treatment cycle. Each fogging device 31 illustratively includes a portable housing 32, and an atomizing fluid generator carried by the housing and including a fluid reservoir 33 carried by the housing, a compressor 34 carried by the housing and coupled to the fluid reservoir, and an atomizing nozzle 35 carried by the housing and in fluid communication with the fluid reservoir. The fogging device 31 further includes a first wireless transceiver 36 carried by the housing, and a first processor 37 carried by the housing and coupled to the compressor and the wireless transceiver.

The fogging device 31 may provide several advantages over conventional devices, in that it is relatively compact, rugged, and portable. In one example implementation, each fogging device 31 may provide an atomized solution of chemical to disinfect enclosed areas up to 10,000 square feet for a one gallon fluid reservoir, although the size of the fogging device 31 and reservoir may be changed for treatment of areas of different sizes. By way of example, the fogging device 31 may be used in medical, mold remediation, commercial and residential applications, as well as other areas. Furthermore, in addition to disinfecting, deodorizing, preserving, or sterilizing applications, the fogging device 31 described herein may also be used for other applications such as the delivery of pesticides (e.g., for termite, mosquito, bedbug, or general pest prevention chemicals). In some embodiments, the fogging device 31 may also be used in a semi-enclosed or open area, in addition to treating enclosed areas.

The housing or case 32 of the fogging device 31 may be a relatively compact and rugged rotomolded construction, and in the illustrated example it includes molded banding along the bottom and top of the unit encompassing one or more round air intakes 40 (although air intake or exhaust ports may be located at different locations on the housing). The fogging device 31 also illustratively includes cut-outs for power entry 41, an output(s) 42 (e.g., an electrical AC outlet), and associated circuit breaker 43. A fill cover 48 (FIG. 1) is over an integrated funnel 44 (FIG. 2B), which leads to the chemical solution reservoir 33 (e.g., a one-gallon reservoir, although other sizes may also be used). By way of example, feet 45 (e.g., rubber) may be coupled to the bottom of the housing 32 (four are shown in the example embodiment, although other numbers may be used in different embodiments). Cord wraps (made of injection mold) may be used to stow the power cord in some embodiments, if desired.

The form factor of the fogging device 31 allows for relatively easy transportation, as well as stability during transport. An integrated handle 46 also allows for ease of carrying. In the example embodiment, the total size of the unit is 19¾" long×14½" wide by 17¼" high, although different dimensions and case shapes may be used in different embodiments. Metal reinforcing mounting plates may also be used inside the housing 32 to mounting the various internal components and increase ruggedness and structural integrity.

Figure 5:
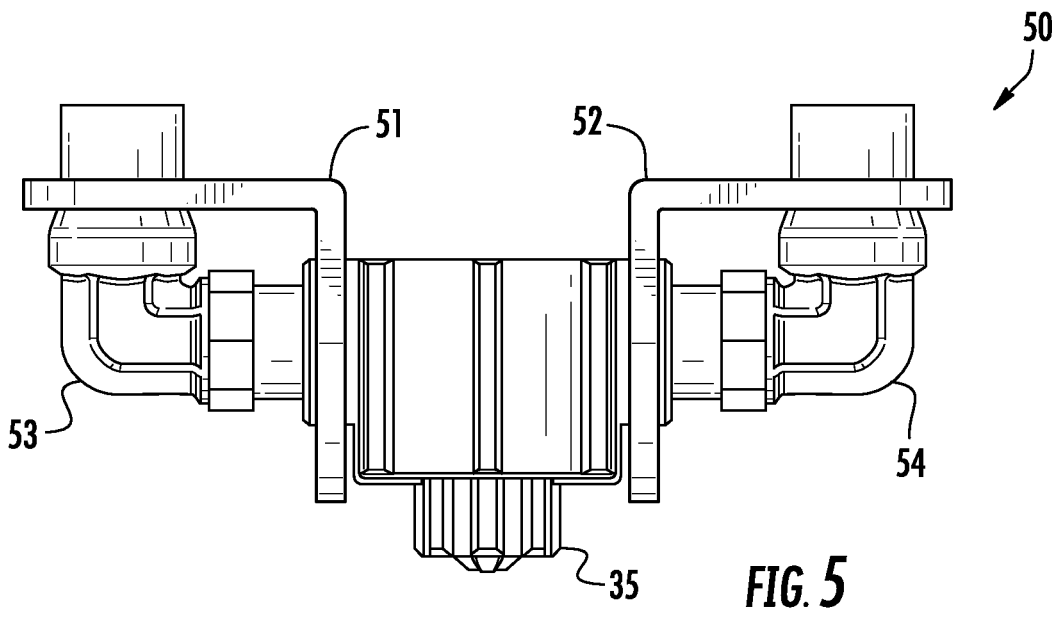
FIGS. 5 and 6 are top and side views, respectively, of an example nozzle assembly for the fogging device of FIG. 1.
Figure 6:
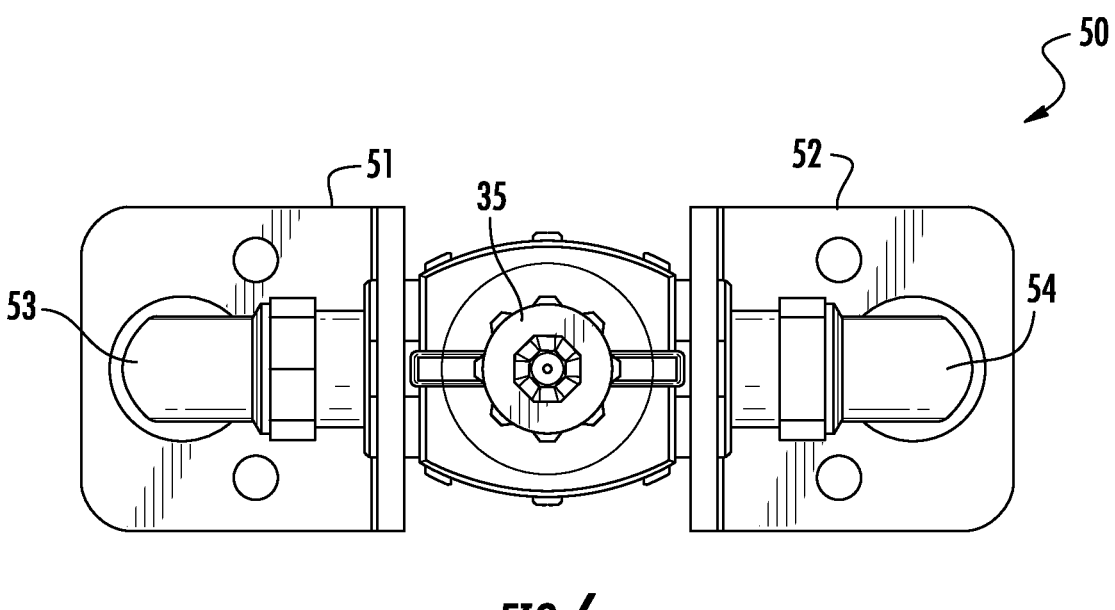
Figure 7:
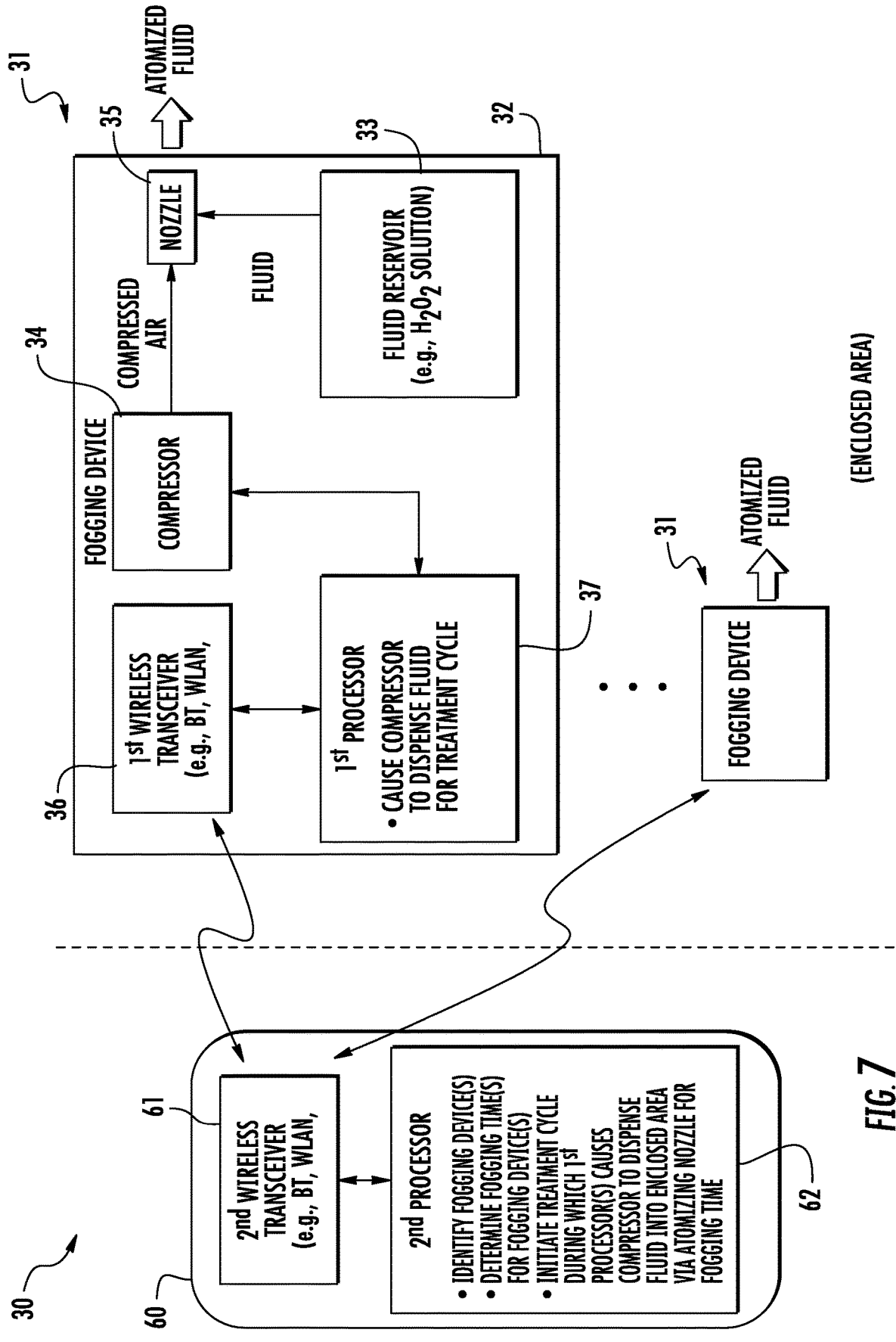
FIG. 7 is a schematic block diagram illustrating a system for treating an enclosed area with an atomized fluid which may include a plurality of the fogging devices of FIG. 1.

The atomizing nozzle 35 is carried by a nozzle holder assembly 50, which allows the nozzle to be adjustable to multiple dispensing positions ranging from vertical to horizontal (although a greater range of adjustability than 90° may be used, if desired). That is, the nozzle holder assembly 50 advantageously allows fogging vertically or horizontally as conditions require. More particularly, the nozzle holder assembly illustratively includes two "L" shaped or 90° brackets 51, 52 with a hole through each side or leg of the bracket. The holes in the bracket 51 allow a feed pipe 53 to supply compressed air from the compressor 34 to the atomizing nozzle 35, while the holes in the bracket 52 allow a feed pipe 54 to supply chemical fluid from the fluid reservoir 33 to the atomizing nozzle 35 (FIGS. 5 and 6). In some embodiments, an optional filter may also be connected in-line between the fluid reservoir 33 and the atomizing nozzle 35. The nozzle 35 is pivotally coupled to the brackets 51, 52 to allow the above-noted rotation from horizontal to vertical orientations (or otherwise), as desired. The fluid reservoir 33 may optionally include a vent, such as with barb fitting, for example. In some embodiments a strap may be used to add further stability to the fluid reservoir 33 within the housing 32, although this is not required in all configurations.

In some embodiments, an actuator may be included that is controlled by the first processor 37 to move the nozzle 35 during the treatment cycle for enhanced fog circulation, if desired. Also, in other embodiments, more than one atomizing nozzle 35 may be used, as well as different mounting configurations, along with an appropriately sized compressor to provide increased atomized spray output. One example atomizing nozzle 35 which may be used is part no. 1/4J-SU2A from Spraying Systems Co. of Wheaton, Illinois, for example, although other suitable atomizing nozzles may be used in different embodiments. Moreover, different atomizing nozzles may be interchanged for different chemicals, and in some embodiments the processor 37 may accommodate different treatment schedules and/or parameters (e.g., times, pressures, etc.) for different nozzles and treatment chemicals, to allow use of the same fogging device 31 for a variety of different treatment applications. Such treatment schedules and/or parameters may be implemented at the time of manufacture of the fogging device 31, as well as by firmware updates at a later time, as will be discussed further below.

The fogging device 31 may be assembled with the fluid reservoir 33 and compressor 34 being riveted to the interior of the case or housing 32 (although other suitable connectors, such as screws, bolts, etc., may also be used). Recessed rotomolded groves may also be provided in the case for side panel attachment, if desired.

In the illustrated example embodiment, the outlet 42 is a 120V outlet to plug in an air scrubber/filter or dehumidifier to aid in shortening the time required to clear the disinfected area after application of the chemical disinfectant solution, as will be discussed further below. The outlet on/off power may be sequenced by the processing circuitry, i.e., the first processor 37, carried on the included circuit board(s) (not shown), for example. The processing circuitry may be implemented using a combination of hardware (e.g., microprocessors, etc.) and a non-transitory computer-readable medium having computer-executable instructions for causing the processing circuitry to perform the various control operations for the fogging system. One or more case fans 55 may also be provided to aid in housing and compressor cooling, which may also be controlled by the processing circuitry.

By way of example, the first wireless transceiver 36 (which may also be carried on an internal circuit board) may be a Bluetooth, Wi-Fi (WLAN), WiMax, cellular, or other suitable wireless transceiver which may be used to wirelessly interface the first processor 37 with other fogging devices 31, wireless humidity sensors, wireless filters or dehumidifiers, as well as one or more mobile wireless communications devices 60 (e.g., smart phones, tablet computers, laptops, etc.). In the illustrated example, the wireless communications device 60 is a smart phone including a second wireless transceiver 61 and a second processor 62. With reference to the flow diagram 140 of FIG. 14, beginning at Block 141, the second processor 62 may be programmed to identify the plurality of fogging devices 31 within the enclosed area based upon the first and second wireless transceivers, at Block 142. In accordance with one example implementation shown in FIG. 8, the second processor identifies that there are four fogging devices 31 within wireless communication range which have serial nos. 1234, 1235, 1236, and 1237 as indicated on a display 63 of the mobile wireless communications device 62.

In addition to an identifier (e.g., serial no.) of the identified fogging devices 31, various other types of information or events for each fogging device may also be provided to the wireless communications device 60, including a status of each fogging device 31, a time left in the fogging cycle, etc. For example, treatment cycle status information may be provided, such as when the treatment cycle has been initiated, how much treatment time left, and when the treatment cycle is complete. Another event is when the treatment area is safe to enter. For example, the treatment area may be safe to enter after a delay period following treatment. In another example, the treatment area may be safe to enter after an associated air filtering or dehumidification process is complete following treatment, as will be discussed further below. An audible alarm may also be provided to indicate one or more of the following events. Moreover, other information which may be communicated to/from the fogging system may include start/stop commands, a pause or delay command, updated status requests, tank fill level, operating temperature, etc., for example.

In another example shown in FIG. 9, the mobile wireless communications device 60 may allow a user to input certain parameters associated with the treatment job to be performed. In this example, an operator's name (here "Frank") may be provided, along with a name of the building or job site ("St. Mary's Hospital"), a room number of the job ("345"), the dimensions and/or volume of the room to be treated, a target humidity level (here 95%), as well as fog time (here 30 minutes) and pulse time (here 15 minutes). Moreover, these settings may also be saved in memory as a job and assigned a respective number (here job #35) so that the next time a treatment is performed the job particulars need not be input again.

For the present example where multiple fogging devices 31 are present in the enclosed treatment area, the second processor 62 may determine respective fogging times for the plurality of fogging devices based upon a size of the enclosed area and the number of fogging devices identified within the enclosed area, at Block 143. More particularly, multiple fogging devices 31 may advantageously be used in conjunction for the treatment of larger areas, or to expedite the treatment of a smaller more critical area that needs to be turned around quickly (e.g., an operating room, etc.). Knowing the fluid dispensing rate of the fogging device 31 for a given chemical, the desired saturation level, and the size (e.g., entered volume or volume calculated based upon the entered room dimensions), the second processor 62 may calculate the respective times that the fogging device will need to run continuously to reach the desired saturation level. Generally speaking, the desired saturation level may be selected so that the concentration of the chemical is at a maximum level before condensation begins on surfaces in the enclosed area.

In the present example, each fogging device 31 will only need to run ¼ of the time it otherwise would if it was the only fogging device in the enclosed area (since there are four fogging devices). Generally speaking, each fogging device 31 will be assigned an equal treatment or fogging time, but in some embodiments different devices may be assigned different fogging times. This could be based upon different fluid levels in each of the fogging devices 31, different flow rates of the identified fogging devices, operational hours on each fogging device, etc.

Moreover, respective pulse times may also be assigned to each fogging device 31. During a pulse cycle, the fogging device may cycle on and off to help keep the enclosed area at the desired humidity level without oversaturating the enclosed area. Moreover, this may also help to conserve treatment fluid. When multiple fogging devices 31 are being used, their pulse times may be coordinated to be on (i.e., dispensing fluid) at the same time, or to turn on at different (staggered) times, if desired.

Once the fogging times are determined for the fogging devices 31, the second processor 62 may initiate a treatment cycle during which, on a coordinated schedule, the first processor 37 of each fogging device 31 causes its associated compressor 34 to dispense fluid from the fluid reservoir 33 into the enclosed area via the atomizing nozzle 35 for the respective fogging time of the fogging device, at Block 144. The fogging devices 31 may then run for the designated fogging times in a continuous mode so that the enclosed area reaches the desired saturation level, at Block 145, after which the optional pulse phase may occur for the appropriate amount of time, at Block 146, which illustratively concludes the method of FIG. 14 (Block 147). In the example implementation shown in FIG. 9, a H$_2$O$_2$ fogging solution (i.e., a mixture of H$_2$O$_2$ and water) is used for a disinfection treatment in a hospital room, with a desired saturation level of greater than 85%, and more particularly between 90 and 95%, although other types of treatment chemicals and appropriate saturation levels may be used for different applications in different embodiments. An example pulse phase for this use case may be 45 seconds on, 15 seconds off during each minute of the pulse phase, although other cycle times may be used in different embodiments.

Generally speaking, Applicant theorizes without wishing to be bound thereto that during the fog or saturation phase, enough chemical should be added to the enclosed area to bring the area to around 90% relative humidity or more for the above-described H$_2$O$_2$/H$_2$O mixture. More particularly, with such a chemical mixture, when the relative humidity is above 85% then the enclosed area may be considered to be in the "kill zone" where most if not all pathogens will be killed if exposed for a sufficient duration at this concentration. Thus, the amount of time necessary for the fog or saturation cycle may vary depending on the starting relative humidity, and additional time may be required where the starting humidity is relatively low, for example, to reach the kill zone. The purpose of the pulse phase is to keep the enclosed area in the kill zone.

In accordance with another example dwell cycle implementation, the pulse phase may be broken into five minute programmable segments (although other durations may also be used). Each segment may include compressor cycling on/off for a given time (e.g., 100 seconds off, 100 seconds on, 100 seconds off, although other durations may be used and the on/off times may be different). This ratio may change based upon the given fog or saturation time. That is, for a shorter fog time there may be a shorter ON segment, and a longer fog time may have a longer ON segment, for example. The length of the pulse time may advantageously be adjusted (e.g., in a range of 10 to 40 minutes, although longer or shorter times may be used) based upon the particular pathogen(s) that is targeted. By way of example, a relatively short pulse phase of ten minutes may be sufficient for a relatively easy to kill pathogen, while a longer time (e.g., 25 minutes or more) may be used to kill C-Difficile (C. diff).

Figure 10:
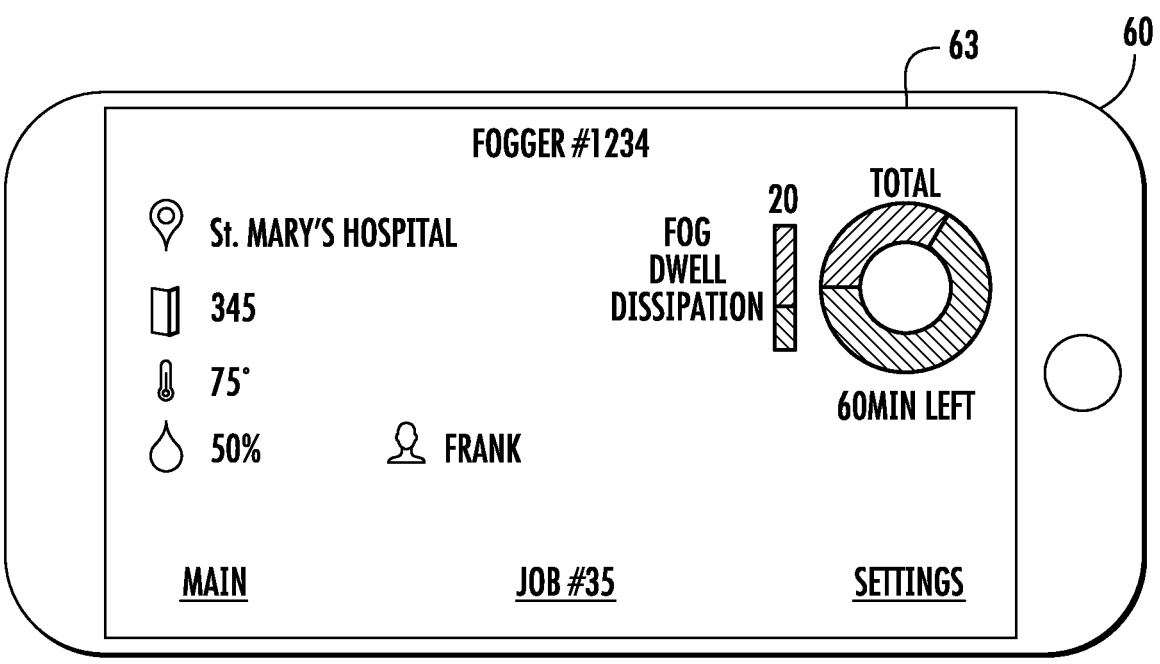

FIG. 10 shows an example screen shot during a treatment cycle indicating the status of the job being performed for the specific fogger with serial no. 1234. Here again, the building/room information and technician name are displayed, along with other parameters relating to the status of the job. More particularly, a temperature measured by an optional temperature sensor (not shown) of the fogging device 31 is displayed, a current measured humidity level is being displayed (which may be determined by a humidity sensor located in the room, as will be discussed further below, although there may be a humidity or micro-condensation sensor on the fogging device as well), as well as indicators of progress in the treatment cycle and time remaining. In should be noted that the screen shot of FIG. 10 may be based upon "real time" data when the first and second wireless transceivers 36, 61 are in range of one another, but the second processor 62 may also provide virtual or estimated information if the wireless transceivers are out of range. That is, the second processor 62 may keep its own estimated times to completion for each fogging device(s) 31, which is updated when in wireless communications range of the fogging device. Thus, if a technician leaves the vicinity of the enclosed area during the treatment cycle, he may still know the approximate status of each fogging device(s) 31 even though it is presently out of range.

In accordance with one example implementation, the plurality of fogging devices 31 may be wirelessly "daisy-chained" or otherwise connected together in a wireless network (e.g., an ad-hoc Wi-Fi network) to coordinate start/stop times for application to larger spaces. For example, an ad-hoc network may be established between a plurality of fogging devices 31 in one or more rooms of a building, etc., such that the wireless communications device 60 acts as a master device to coordinate start/stop times of the other devices between them (which act as slave devices). In this regard, the wireless communications device 60 may be a smart phone, tablet, etc., as noted above, or in other embodiments the wireless communications device may be a given fogging device 31 from which the treatment cycle is initiated for all of the remaining devices. In another example embodiment, the wireless communications device 60 (e.g., a smart phone, tablet computer, etc.) may pair with each of the fogging devices 31 individually (e.g., via Bluetooth), and cause them to start sequentially (i.e., one after the next), or to all begin fogging at the same time, for example. Thus, start/stop times for the different fogging devices 31 may be coordinated to occur at the same time, or to be staggered, as desired for a given implementation.

Figure 11:
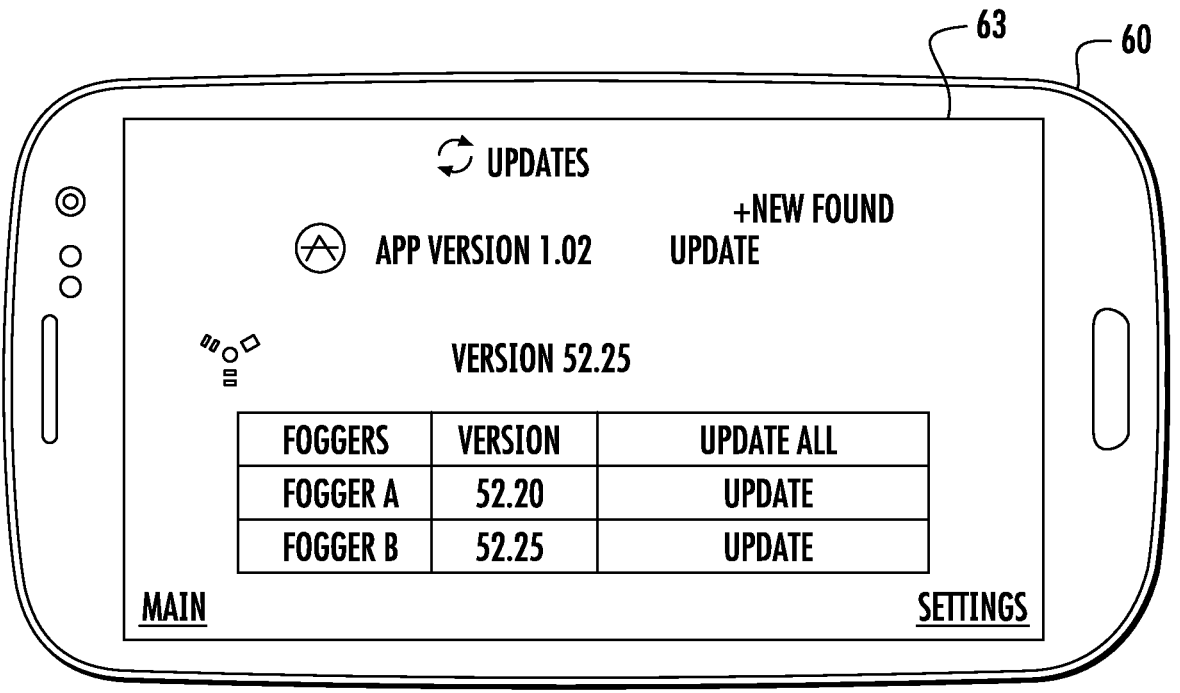

Referring additionally to FIG. 11, in some embodiments the wireless communications device 60 may be further programmed to provide firmware updates (e.g., retrieved via the Internet from the manufacturer) to the first processors 37 of each fogging device 31 via the first and second wireless transceivers 36, 61. In the illustrated example, two fogging devices 31 are identified (here labeled Fogger A and Fogger B), along with an indication of the firmware version that each is running (52.20 and 52.25, respectively). Moreover, a most current version of the firmware currently available (here version 52.25) is also provided, along with a selection button or link to download or push the update to the given fogging device 31. Moreover, this illustrated screen also provides an indication of the version of the app running on the mobile wireless communications device 60 (here version 1.02), along with a link or button that may be selected to update the app version.

The app may be provided by the manufacturer of the fogging devices 31 for users to install on different computing platforms (e.g., Android, iOS, etc.), and allow for future firmware upgrades to the fogging devices including, but not limited to, support for optional hardware (humidity sensors, $H_2O_2$ sensors, etc.), new treatment cycle profiles for different chemicals, etc. Similarly, the app may provide corresponding control options for such features on the display 63. The app may also display operational hours, maintenance issues, malfunctions, etc., which may occur with the fogging devices as well. Such information may be maintained by the first processor 37 of each fogging device 31 and locally stored, and it may be accessed via respective control panels 49 at each of the fogging devices as well. The control panel 49 may include a digital (e.g., LED) display and one or more input devices (e.g., buttons, knobs, etc.), for example. The app may also cause the first processor 37 to provide updates regarding usage and status of each fogging device 31 to a central location (e.g., manufacturer, service company, etc.) so that maintenance needs and job performance may be monitored, for example.

Figure 12:
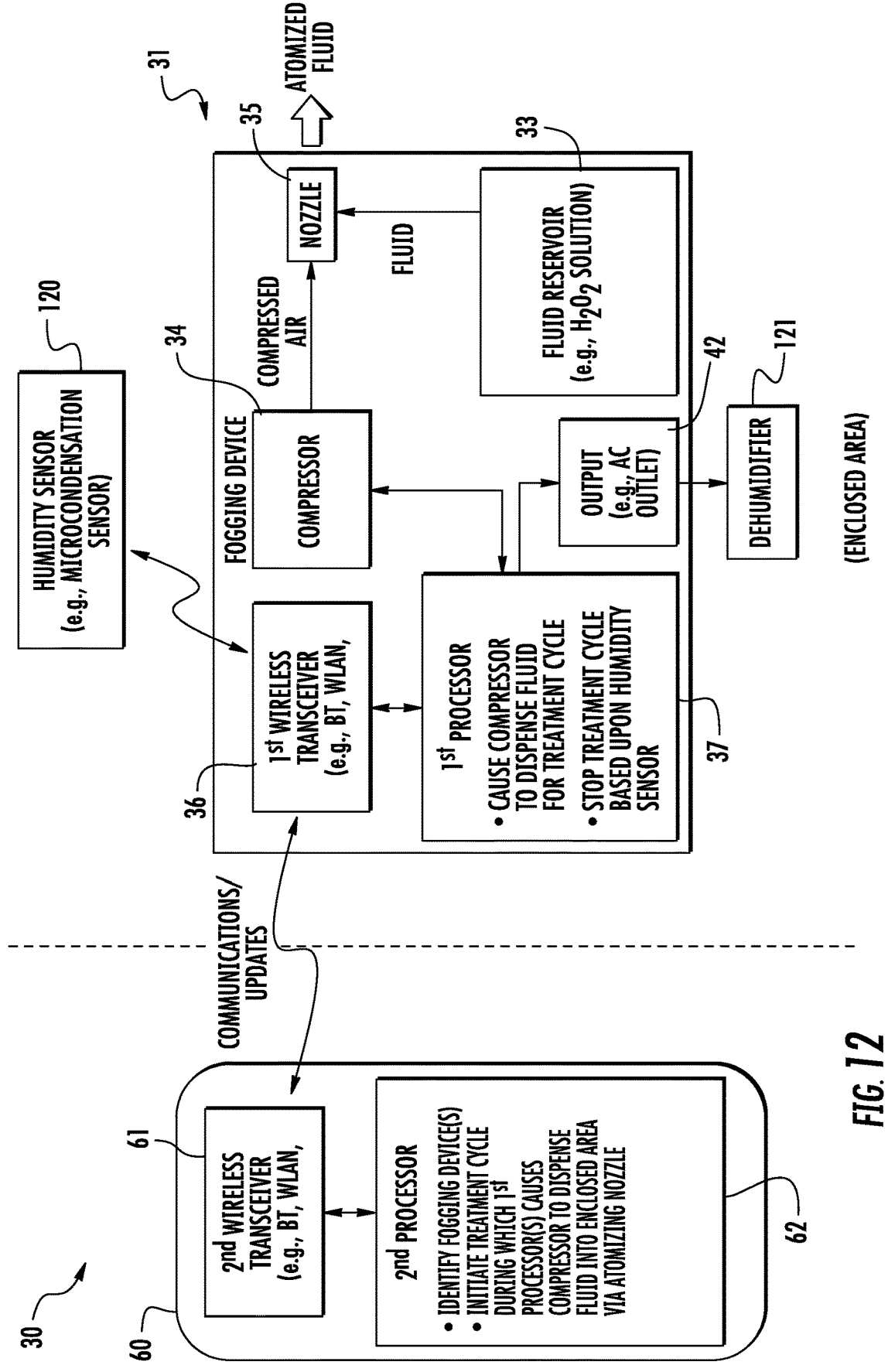
FIG. 12 is a schematic block diagram illustrating a system for treating an enclosed area in accordance with another example embodiment.
Figure 15:
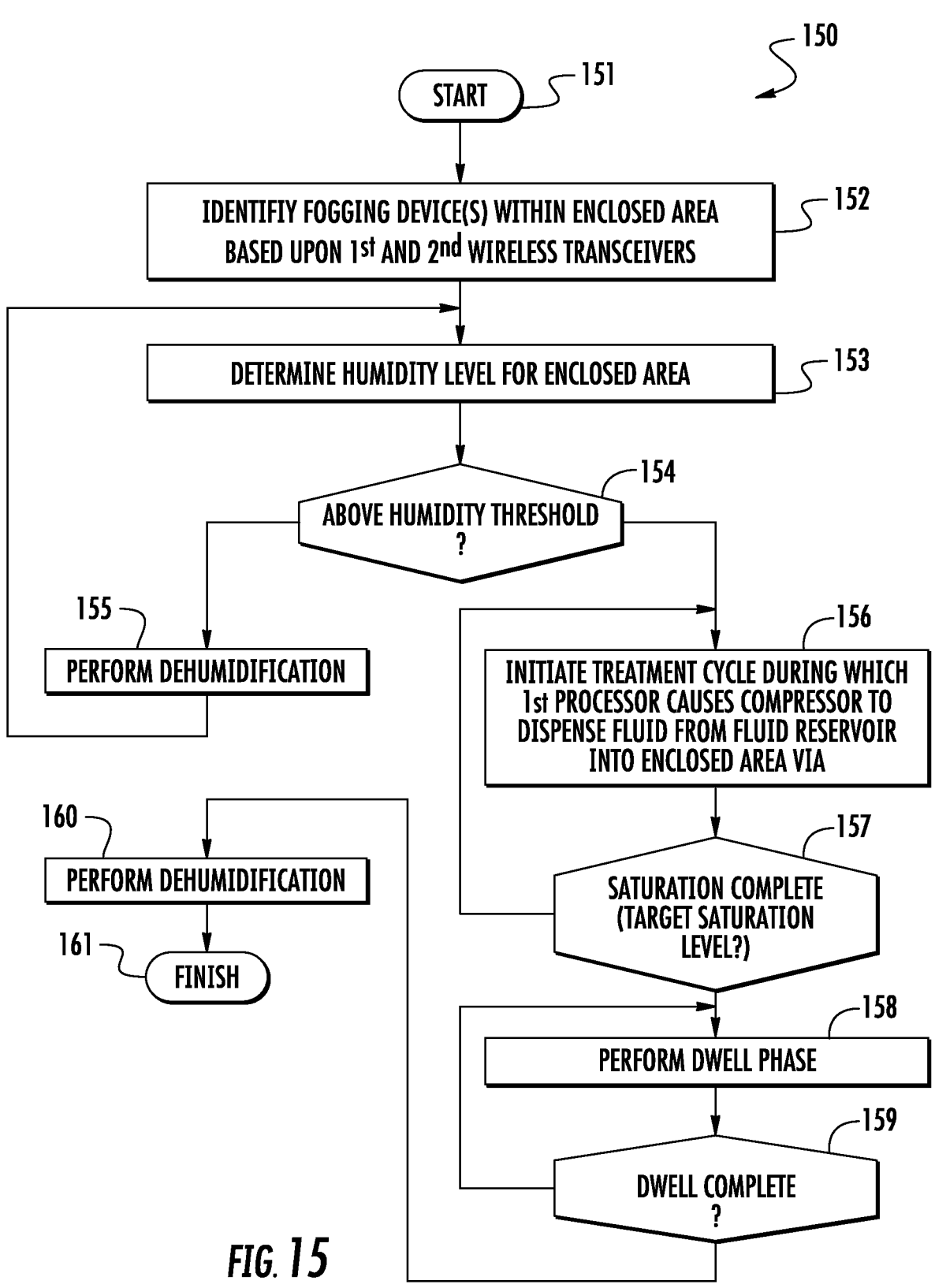
FIG. 15 is a flow diagram illustrating method aspects associated with the system of FIG. 12.

Turning now to FIGS. 12 and 15, in accordance with another example embodiment, a fogging device(s) 31 may be paired with a humidity sensor 120 for monitoring the humidity level in the enclosed area to control the fogging treatment cycle. In one example embodiment, the humidity sensor 120 may be a micro-condensation sensor, for example, although other types of humidity sensors may be used in different implementations (e.g., a $H_2O_2$ sensor, where are $H_2O_2$ treatment chemical is being used). In some applications, it may be desirable to place the humidity sensor 120 in the enclosed area apart from the fogging device 31, as illustratively shown in FIG. 12, to help ensure that the humidity reading more accurately reflects that of the overall area. However, in other applications the humidity sensor 120 may be incorporated or integrated in the fogging device 31 itself. In particular, if the nozzle 35 is directed out and away from the fogging device 31 (i.e., rather than straight up in the air), a built in humidity sensor 120 may provide desired readings as well. In such case, the humidity sensor 120 may be directly connected or hard wired to the first processor 37.

Beginning at Block 151 in the flow diagram 150, the fogging device 31 may be identified by the wireless communications device 60 as described above, at Block 152 (although in some embodiments the fogging device may be controlled locally and a separate wireless communications device need not be used to interface with the fogging device). The first processor 37 of the fogging device 31 may communicate with the humidity sensor 120 via the first wireless transceiver 36, although a wired link may also be used in some embodiments. The first processor 37 may thereby determine an initial humidity level for the enclosed area prior to the beginning of the treatment cycle, at Block 153.

Generally speaking, for some chemical solutions, greater efficacy may be achieved if the treatment is started when the humidity within the enclosed area is in a preferred or desired range. By way of example, with respect to a 95% $H_2O$ to 5%

$H_2O_2$ disinfectant solution, Applicant theorizes without wishing to be bound thereto that greater efficacy is achieved if the treatment cycle is initiated when a relative humidity in the enclosed treatment area is between 30% and 50%.

To this end, a dehumidifier 121 may optionally be connected to the output 42 of the fogging device 31, and when the first processor 37 determines that the humidity level in the enclosed area is above 50% from the humidity sensor 120, the first processor may accordingly activate the output 42 to turn on the dehumidifier until the humidity level falls below the desired humidity threshold (here 50%, although other levels may be used in different applications), at Blocks 154-155. Conversely, in extremely dry climates, a humidifier may likewise be connected to the output 42 to perform humidification and raise the starting humidity for the enclosed area to the desired lower threshold for the effective starting humidity range (e.g., 30% in the above example). It should be noted that while the output 42 was described as an AC outlet above, in some embodiments this could be a low power output (e.g., USB port, etc.), or the humidifier, dehumidifier, filter, etc. may be controlled wirelessly, similar to the humidity sensor 120. In such cases, the dehumidifier (and/or humidifier) may be plugged into its own wall outlet, so that it need not receive power from the fogging device 31.

Once the humidity in the room is within the desired starting range (e.g., below 50% in the present example), the treatment cycle may be initiated (Block 156) during which the first processor 37 of the fogging device(s) 31 causes its associated compressor 34 to dispense fluid from the fluid reservoir 33 into the enclosed area via the atomizing nozzle 35, as discussed above. However, in this implementation, a fogging time for the fogging device(s) 31 need not be set or calculated by the second processor 62, as the first processor 37 may instead communicate with the humidity sensor 120 to determine when the humidity level in the enclosed area has reached the target saturation level from fogging (e.g., 90% in the present example), at Block 157.

If a pulse phase is used for the particular treatment, as discussed above, intermittent cycling of the atomizing spray may be performed until the desired pulse time is completed, at Blocks 158-159. Stated alternatively, it is the determination by the humidity sensor 120 that the target saturation level has been reached that triggers stopping of the saturation or fog phase of the treatment cycle, and the beginning of the pulse phase of the cycle (if used in the given embodiment). Again, the pulse time may be based upon the particular chemical being used, and how long the enclosed area needs to remain at the saturation level for the given application. In the above example, the pulse phase may be used to help keep the relative humidity in approximately the 80-95% range (although different target saturation levels and pulse ranges may be used for different types of chemicals). Controlling the treatment cycle based upon measured humidity, rather than a timed cycle, may be helpful in areas where there is a significant amount of drapes, carpet, bedding, etc., which tend to absorb some of the atomized fluid such that a longer saturation phase may be required to get the enclosed area up to the target saturation level as compared to a "bare" room.

In embodiments where the dehumidifier 121 is optionally used, upon completion of the pulse phase the first processor 37 may activate the dehumidifier (Block 160) to help dissipate the chemical in the enclosed area and bring the humidity level back down to a normal level. This may advantageously help make the room safe to enter more quickly than simply waiting for the room to air out. The method of FIG. 15 illustratively concludes at Block 161.

Figure 13:
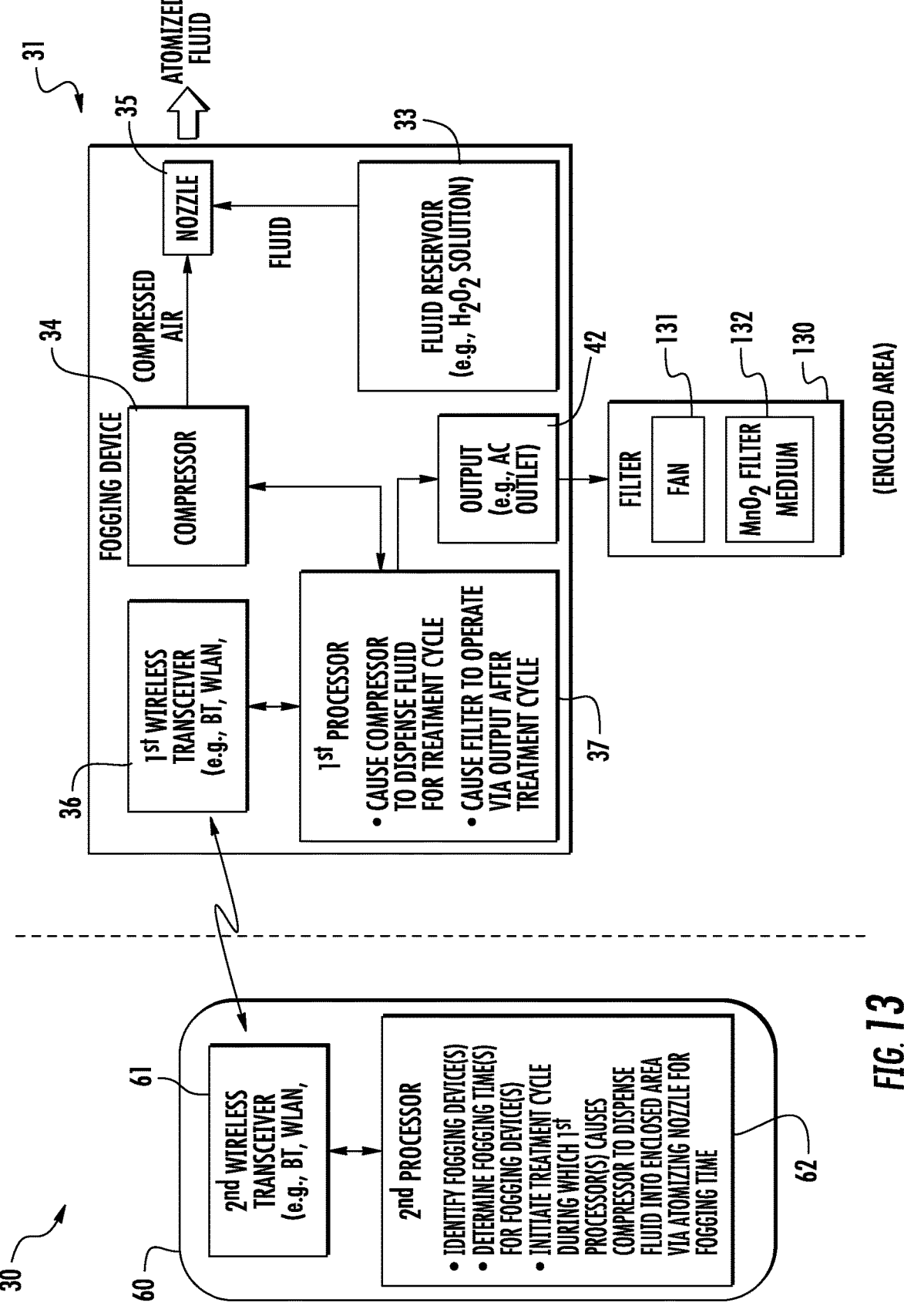
FIG. 13 is a schematic block diagram illustrating a system for treating an enclosed area in accordance with still another example embodiment.
Figure 14:
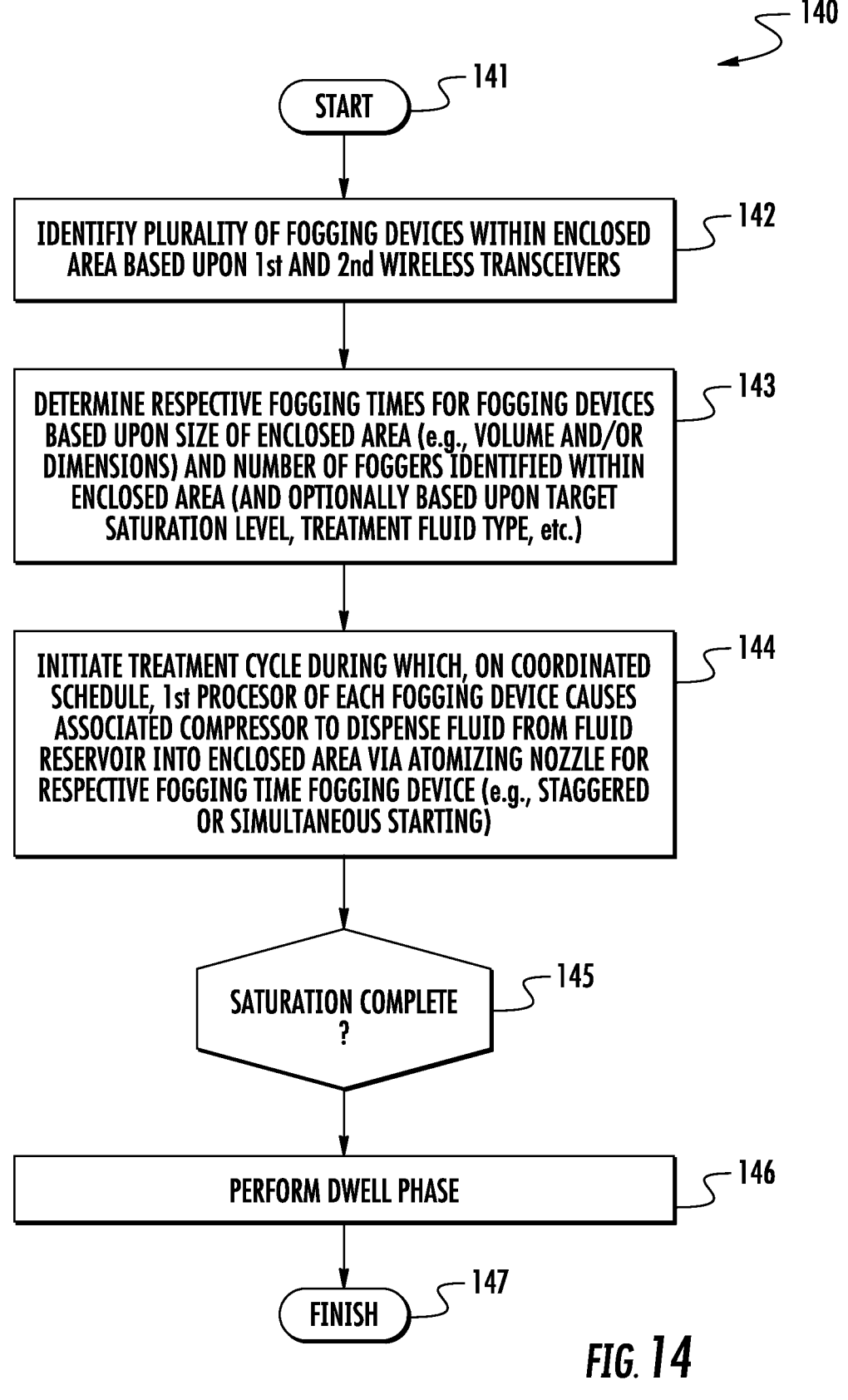
FIG. 14 is a flow diagram illustrating method aspects associated with the system of FIG. 7.
Figure 16:
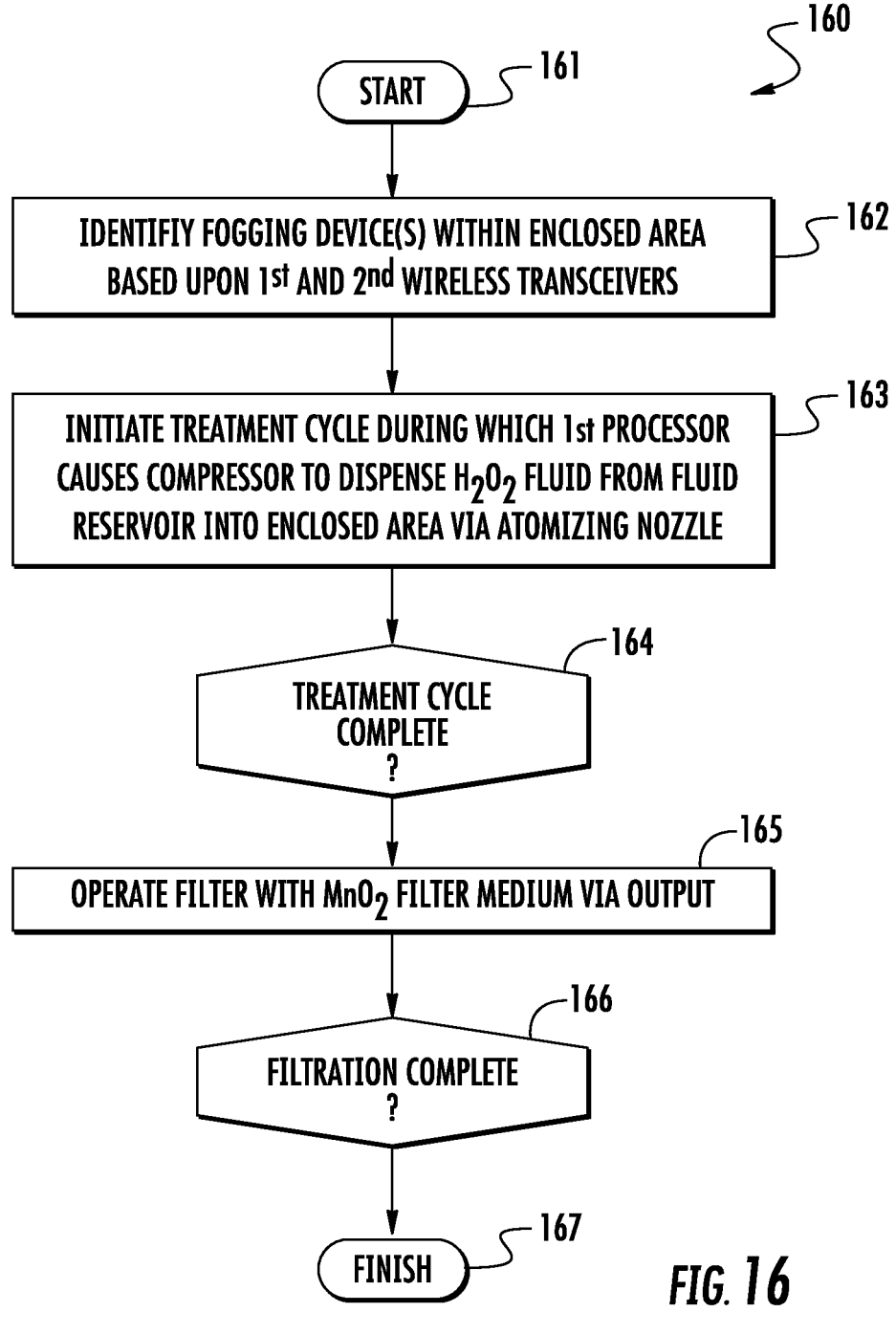
FIG. 16 is a flow diagram illustrating method aspects associated with the system of FIG. 12.

Turning additionally to FIG. 13 and the flow diagram 160 of FIG. 16, another example embodiment is now described in which an optional filter 130 is coupled to the output 42 of the fogging device 31. Beginning at Block 161, The fogging device(s) 31 in the enclosed area may be identified, and the treatment cycle initiated, by the wireless communications device 60 as described above (Blocks 162-163), although it should be noted that a fogging cycle may be initiated directly at the fogging device via the control panel 49 as well without using the wireless communications device in some embodiments. Once the treatment cycle is completed (which may include a saturation phase only, or saturation and pulse phases (as discussed above), at Block 164, the first processor 37 may then operate the filter 130 via the output 42, similar to the way in which the dehumidifier 121 is operated, as described above. The method concludes after the filtration is complete, at Blocks 166-167.

The filter 130 illustratively includes a fan 131 to circulate air through or over a filter medium 132. While various types of filters may be used and coupled to the output 42 of the fogging device 31, for example, for the above-described example of a hydrogen peroxide ($H_2O_2$) based treatment solution, a manganese dioxide ($MnO_2$) filter medium may be particularly helpful to dissipate or neutralize the $H_2O_2$ in the room. Here again, this will more rapidly bring the concentration of the chemical in the room to a level that is safe, allowing the room to be turned around more quickly for its next use. This may be particularly advantageous in areas such as patient rooms or surgical rooms where there is high throughput or demand. Moreover, this approach may be significantly faster than using a comparable portable size dehumidifier. In one example embodiment, the filter medium 132 may include glass beads or pellets which are coated with $MnO_2$, although other suitable styles of filters may also be used, and different chemicals or materials may be used for the filter medium 132 depending upon the given chemical solution that is to be used in the treatment cycle.

In accordance with another advantageous aspect, the fogging device 31 may wirelessly interface with an HVAC system in the building (e.g., such as through a wireless thermostat that has Wi-Fi connectivity, etc.). As a result, the fogging device 31 may control when the HVAC system turns on/off during/after a treatment cycle.

It should be noted that, while various features discussed above are presented individually with respect to different diagrams for clarity of illustration, these features may be combined in a same embodiment in different applications. For example, some or all of the humidity sensor 120, dehumidifier 121, and filter 130 (and/or humidifier) may be used in a same embodiment. Moreover, both time-based treatment cycles and humidity-based treatment cycles may be supported simultaneously. That is, if the humidity sensor 120 is not present in the treatment area, then treatment times may be calculated and used for the fogging device(s) 31, but otherwise the humidity sensor may be used to determine when to start and/or stop the fogging cycle. Furthermore, the treatment times for the fogging device(s) 31 may still be determined even when the humidity sensor 120 is present, in the event that the humidity sensor fails, etc., and the fogging cycle may then be concluded based upon the first processor 37 of the second processor 62 keeping the fogging time as a backup, for example.

Figure 17:
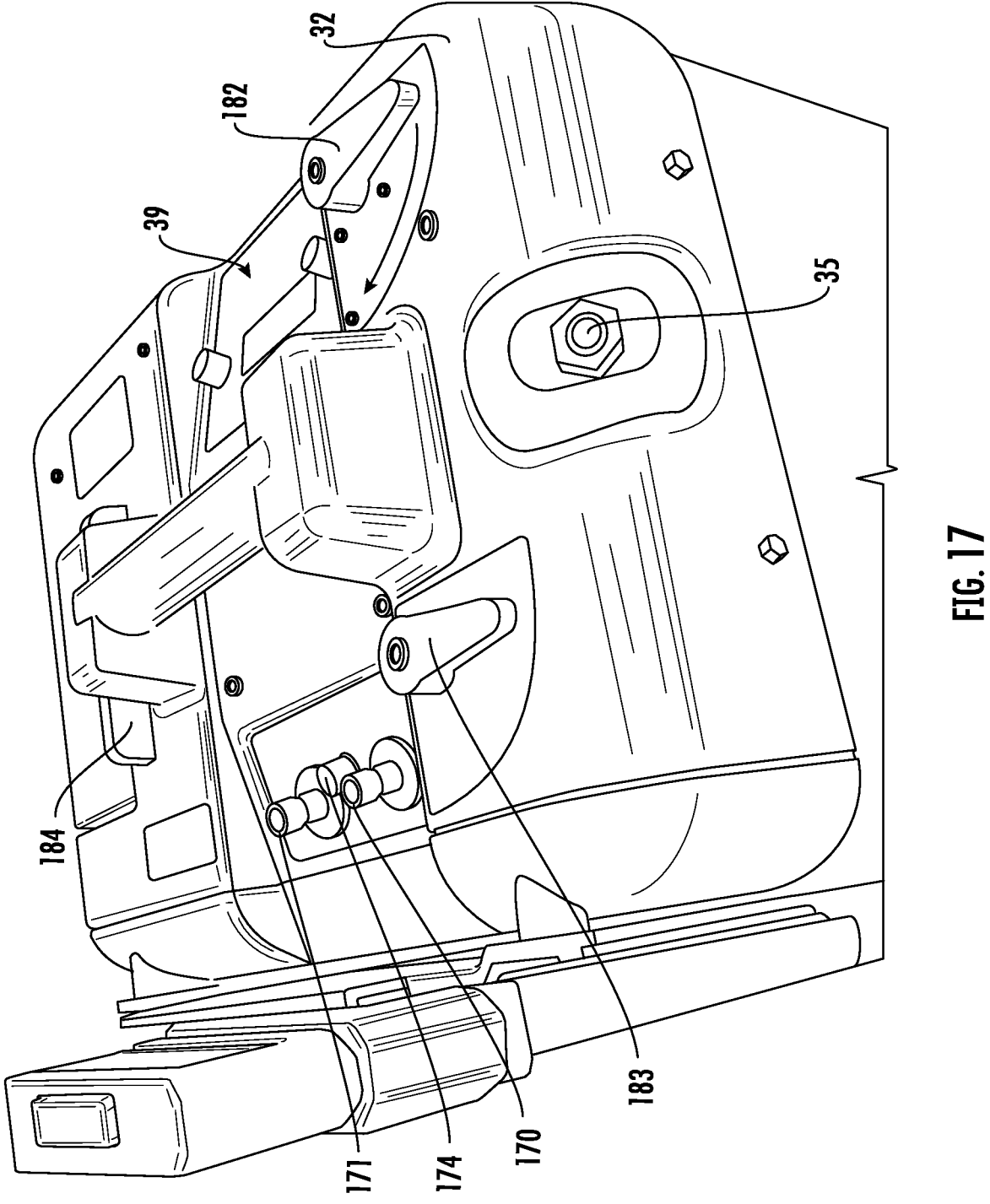
FIG. 17 is a perspective view of another fogging device which has different operational modes for different fogging accessories in accordance with an example embodiment.
Figure 18:
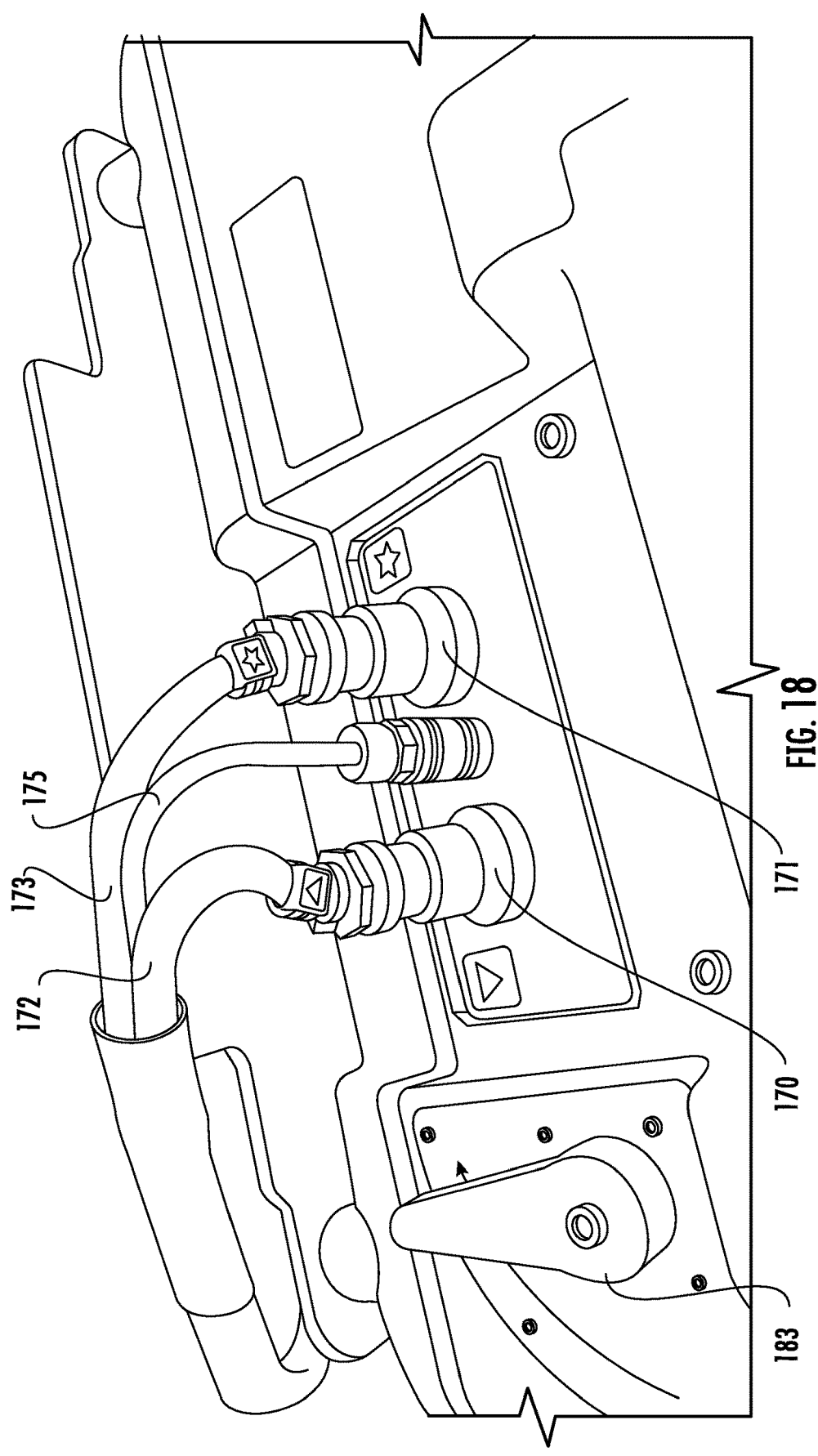
FIG. 18 is a perspective view showing the air and fluid quick-connect ports and data/power port of the fogging device of FIG. 17 in greater detail.

Turning to FIGS. 17-18, another example implementation of the fogging device 31 is now described. The illustrated fogging device 31 includes similar components to those described above, but it further includes quick-connect ports 170, 171 for attaching air and fluid lines 172, 173 of different accessory devices (which will be described further below with reference to FIGS. 19-23) to the compressor 34 and fluid reservoir 33 of the fogging device 31, respectively. In this way, multiple different types of fogging accessory devices may utilize the compressor 34 and fluid reservoir 33 of the fogging device 31, making it a universal and easy to transport platform for numerous fogging applications. Yet, as will be discussed further below, providing a universal platform for multiple accessory devices can be challenging, in that different types of accessories may have different operational parameters that may not work well with or be appropriate for other accessories. The illustrated fogging device 31 is advantageously able to automatically identify the different types of fogging accessories attached thereto, and change its operational modes and associated operating parameters accordingly to match the particular attachment connected to it.

Figure 19:
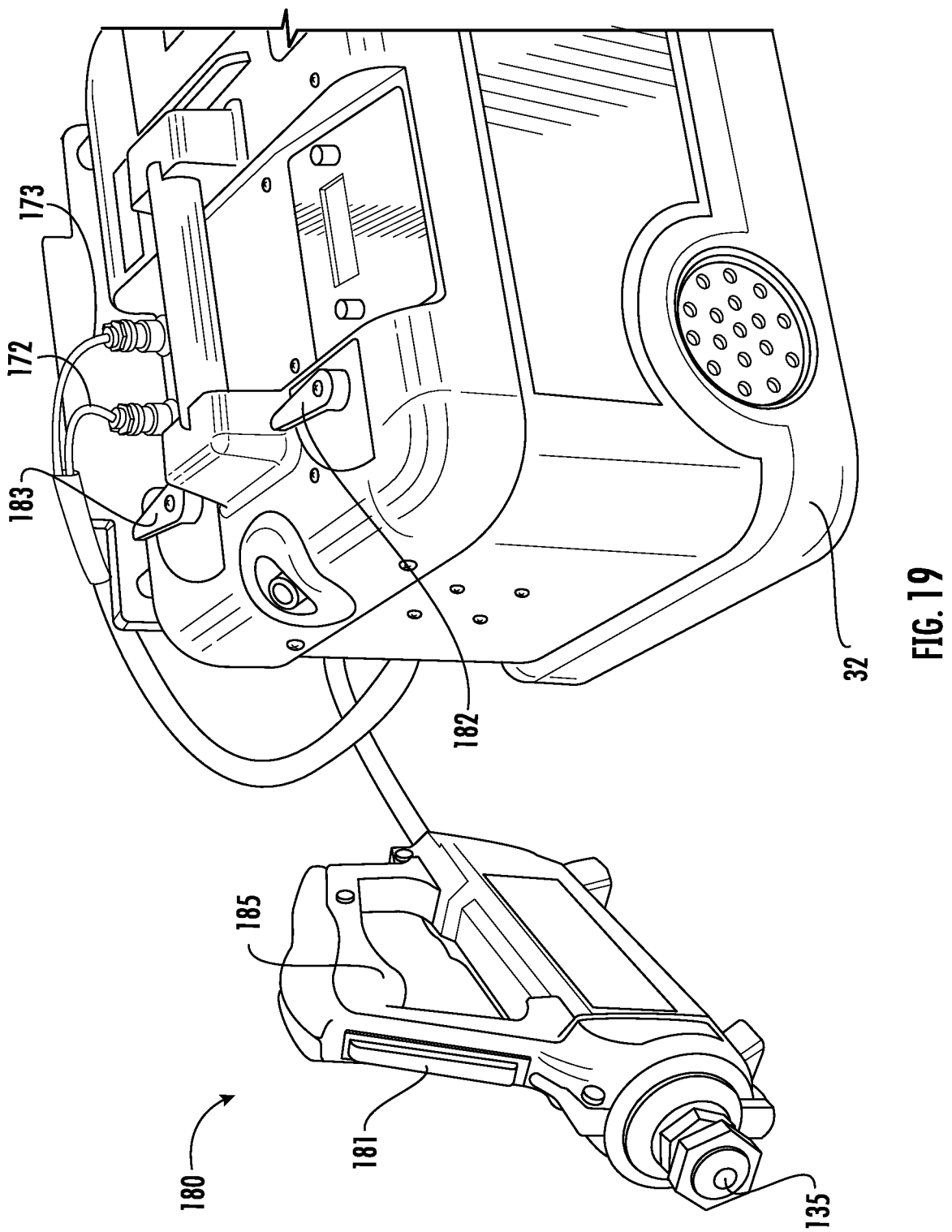
FIG. 19 is a perspective view of hand sprayer accessory which may be used with the fogging device of FIG. 17.

In the example illustrated in FIGS. 18-19, a hand sprayer 180 is connected to the air/fluid quick-connect ports 170, 171. The hand sprayer accessory 180 includes its own atomizing nozzle 135, and its nozzle operates in a similar fashion to the atomizing nozzle 35 carried by the fogging device housing 32. Yet, with the air/fluid cables 172, 173 the hand sprayer 180 can be used to provide a direct atomizing fog spray to surfaces or other locations remote from the fogging device 31 (e.g., on walls/ceilings, in cabinets or other small spaces, etc.). The fogging device 31 further illustratively includes a data/power port(s) 174, and the hand sprayer has a data/power cord 175 that is plugged into the data/power port on the fogging device (see FIG. 18). In some embodiments, the hand sprayer 180 may further include one or more status (e.g., LED) lights 181 that are powered via the power cord 173. Moreover, the hand sprayer 180 also includes electronic circuitry (e.g., a read only memory, etc.) that stores an identifier that identifies what type of accessory the hand sprayer is to the fogging device, which the fogging device reads over the data cord. It should be noted, however, that in some embodiments, a wireless data connection (e.g., Bluetooth, WiFi, RFID, NFC, etc.) could be used to provide the identification data to the fogging device.

The air compressor 34 and fluid reservoir 33 of the fogging device 31 may be selectively switched between the atomizing nozzle 35 carried by the housing 32 (allowing for operation of the fogging device as described above), and the atomizing nozzle 135 of the hand sprayer accessory 180, to thereby switch atomized fluid delivery between the two. In the illustrated example, valve actuators 182, 183 are provided on the exterior of the fogging device 31 to manually operate internal valves to respectively switch the air and fluid flow between the fogging device nozzle 35 and the accessory (here the hand sprayer 180) nozzle 135. However, in some instances the processor 37 may actuate a relay/valve to perform the switch over between the two nozzles 35, 135, e.g., automatically when it recognizes that an accessory is attached, which could be determined based upon reading its identification circuit, for example.

In a default operational mode where the atomizing nozzle 35 of the fogging device 31 is being used to deliver atomized fluid to the treatment space, the data input/control panel 39 of the fogging device 31 may allow environmental parameters such as dimensions and/or cubic area of the treatment space to be entered, for example, as noted above. The fogging device 31 may calculate the appropriate operational times (e.g., for saturation and dwell phases, as described above) and provide a preset or default amount of fluid flow, e.g., 1 oz/minute for the basic fogging device operating mode (although this amount of fluid flow may be manually adjusted in some implementations).

However, when the hand sprayer 180 is connected to the fogging device 31 via the hard-wired connection (or wireless connection in some embodiments), the fogging device recognizes the hand sprayer and switches its mode of operation to a hand sprayer mode. In this mode, the default fluid flow may be higher, e.g., 2 oz/minute, although this again may be adjustable (e.g., from 1.0-3.0 oz/minute), as will be discussed further below. Moreover, in some embodiments, the fogging device 31 may further include a pump 245 (see FIG. 24), and the fogging device 31 operates the pump 245 to prime the sprayer 180 for operation as part of the hand sprayer operating mode. The pump 245 may thereafter be operated to provide the requisite amount of fluid flow (e.g., 2 oz/minute) to the sprayer 180 during operation, as noted above. Other operating parameters may include changing the display on the fogging device 31 to indicate that it is in hand sprayer mode (along with associated hand sprayer operational indicators, such as flow rate, etc., if desired), and to change status indicator operation. For example, status indicator LEDs 184 that would otherwise be operational on the fogging device 31 when its nozzle is in use could be disabled and instead the LED light(s) 181 on the hand sprayer 180 may instead be enabled when the hand sprayer is in use. Moreover, when the fogging device 31 is in the hand sprayer operating mode, air flow control is turned over to the hand sprayer 180, in that the trigger or button 185 on the hand sprayer is what controls the flow of air from the compressor 34 to the hand sprayer atomizing nozzle 135, whereas in its basic operating mode the processor 37 would control when air is delivered to the fogging device 31 atomizing nozzle 35 based upon the programmed treatment cycle for the particular room size/volume being treated, as discussed further above.

Figure 20:
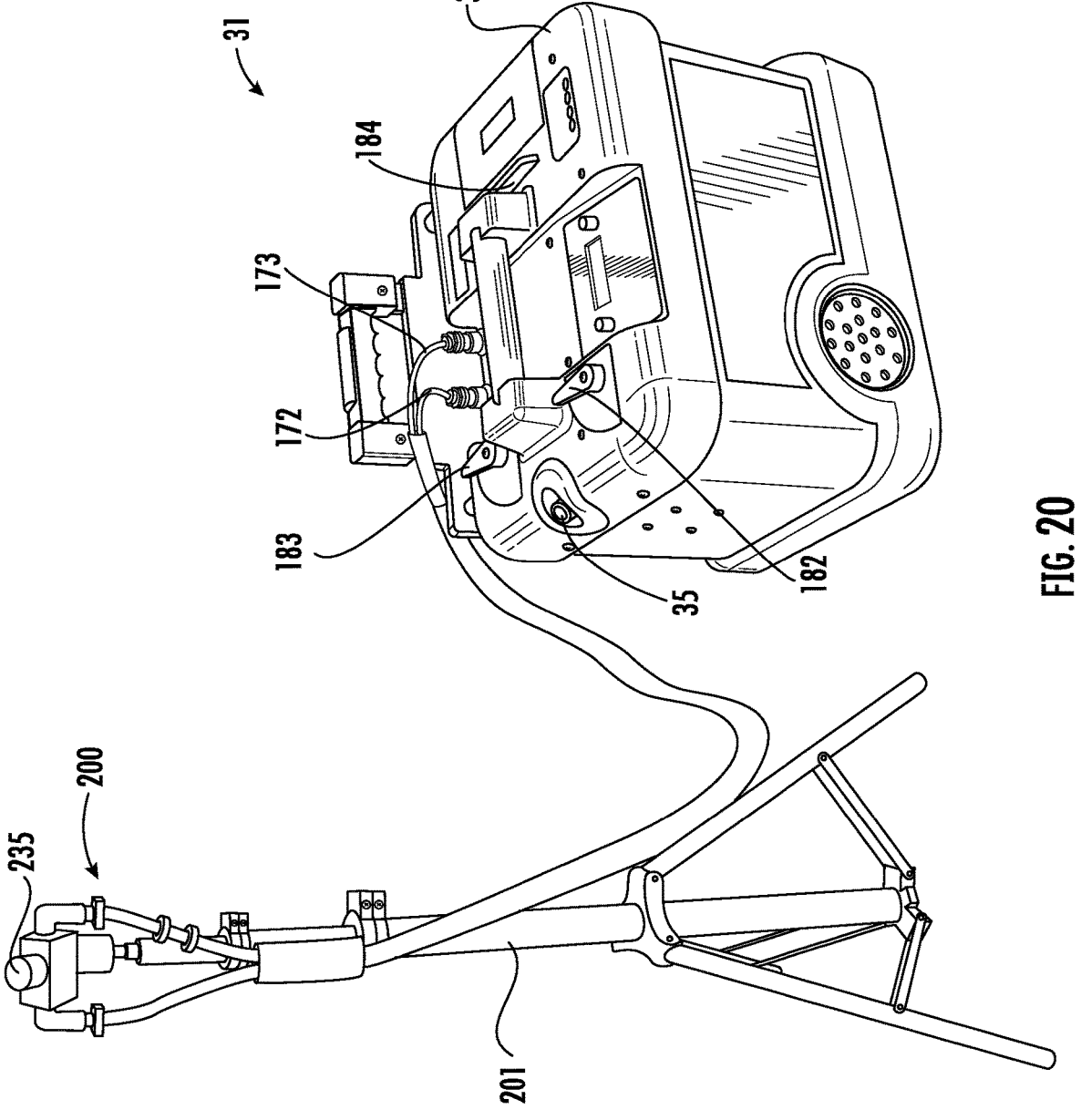
FIG. 20 is a perspective view of an extended nozzle accessory which may be used with the fogging device of FIG. 17.

Another example fogging accessory is shown in FIG. 20, namely an extended nozzle/applicator 200. The extended nozzle 200 is similar to the hand sprayer 180 described above, in that it is a spray head that includes its own atomizing nozzle 235, air/fluid lines 172, 173, and optional data and/or power cord (not shown in FIG. 20). In the illustrated example, the extended nozzle 200 is mounted on a tripod 201, but it may be mounted or positioned using different stands or mounting fixtures in different embodiments. The extended nozzle 200 may advantageously be positioned in remote locations (e.g., in rooms or chambers behind closed doors, in ceiling/attic spaces, etc.) without having to put the fogging device 31 in the same physical location where fogging is to occur.

Figure 21:
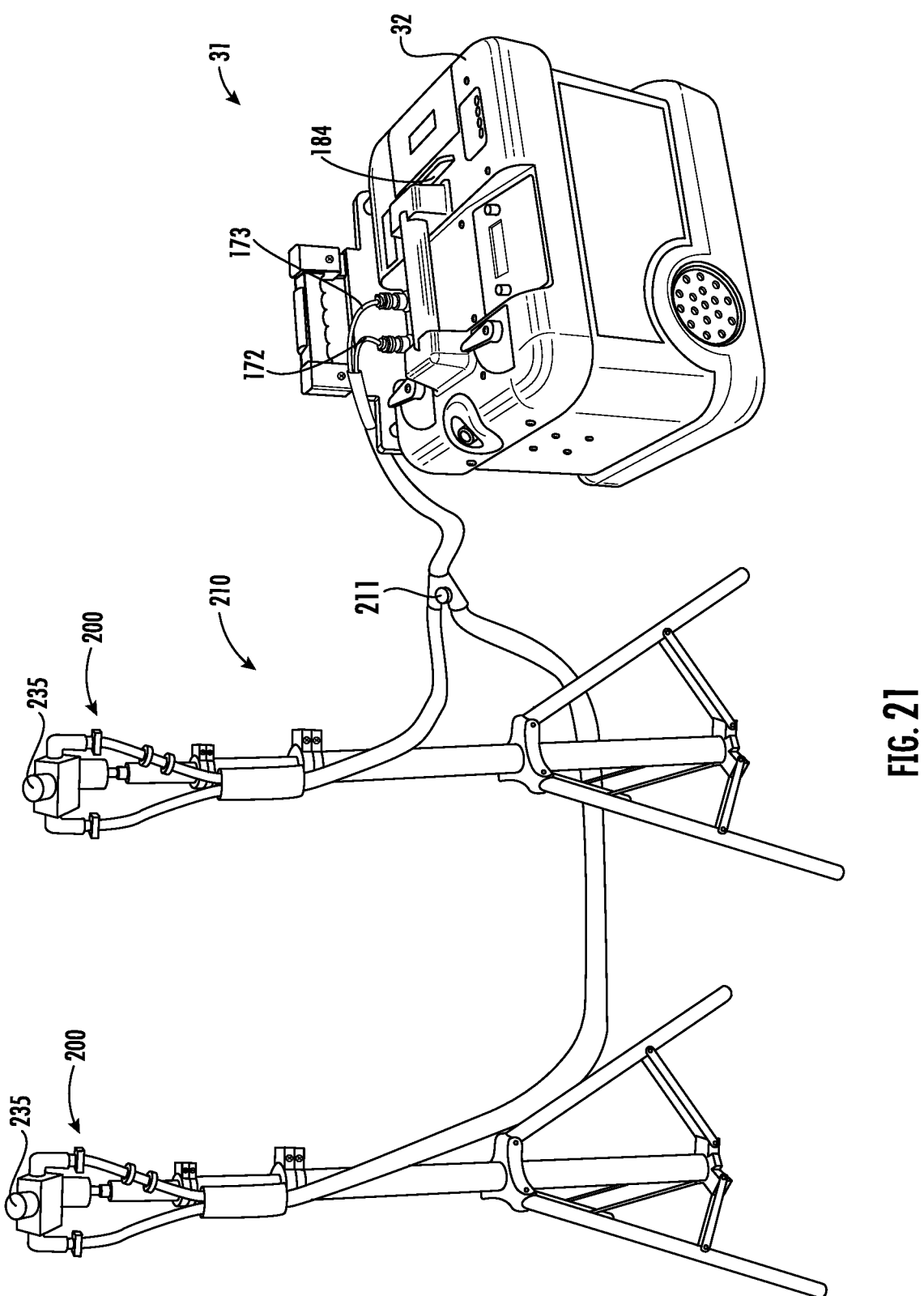
FIG. 21 is a perspective view of a dual extended nozzle accessory which may be used with the fogging device of FIG. 17.

Another similar accessory is shown in FIG. 21, a dual extended nozzle/applicator (dual applicator) 210 which illustratively includes a pair of spray heads 200 each with a respective atomizing nozzle 235 and air/fluid lines, but these air/fluid lines are connected at a junction 211 with main lines 172, 173 that connect to the air/fluid quick-connect ports 170, 171 on the fogging device 31. In this way, the single set of quick-connect ports on the fogging device is able to supply air and fluid to multiple different spray heads 200 at the same time. In this configuration, one or both of the spray heads 200 may carry the circuitry to identify the dual applicator 210 to the fogging device (or the circuitry could be located elsewhere, such as attached to one of the hoses, at the junction 211, etc.).

With regard to the operating modes of the fogging device 31 when the extended nozzle 200 or dual applicator 210 is connected to the fogging device 31, they may include one or more of the parameters and control functions described above with respect to the hand sprayer 180. For example, for the extended nozzle 200, the default flow rate may be similar to that of the fogging device 31 in its basic operating mode, it may involve operation of the pump 245 to prime the extended nozzle, and it may also change the display screen on the fogging device to indicate extended nozzle operation. However, control of the LED indicators 184 need not change (e.g., the LED indicators on the fogging device 31 may still be used to indicate the operational state, such as ready, completed, etc.). Moreover, the fogging device 31 retains control of the air flow based upon its programming for the treatment area. The operational mode of the fogging device 31 with respect to a dual applicator 210 may be different from the single application or extended nozzle 200 in that the fogging device delivers a higher default fluid flow (e.g., 2.5 oz/minute or higher) than for the extended nozzle, for example.

Figure 22:
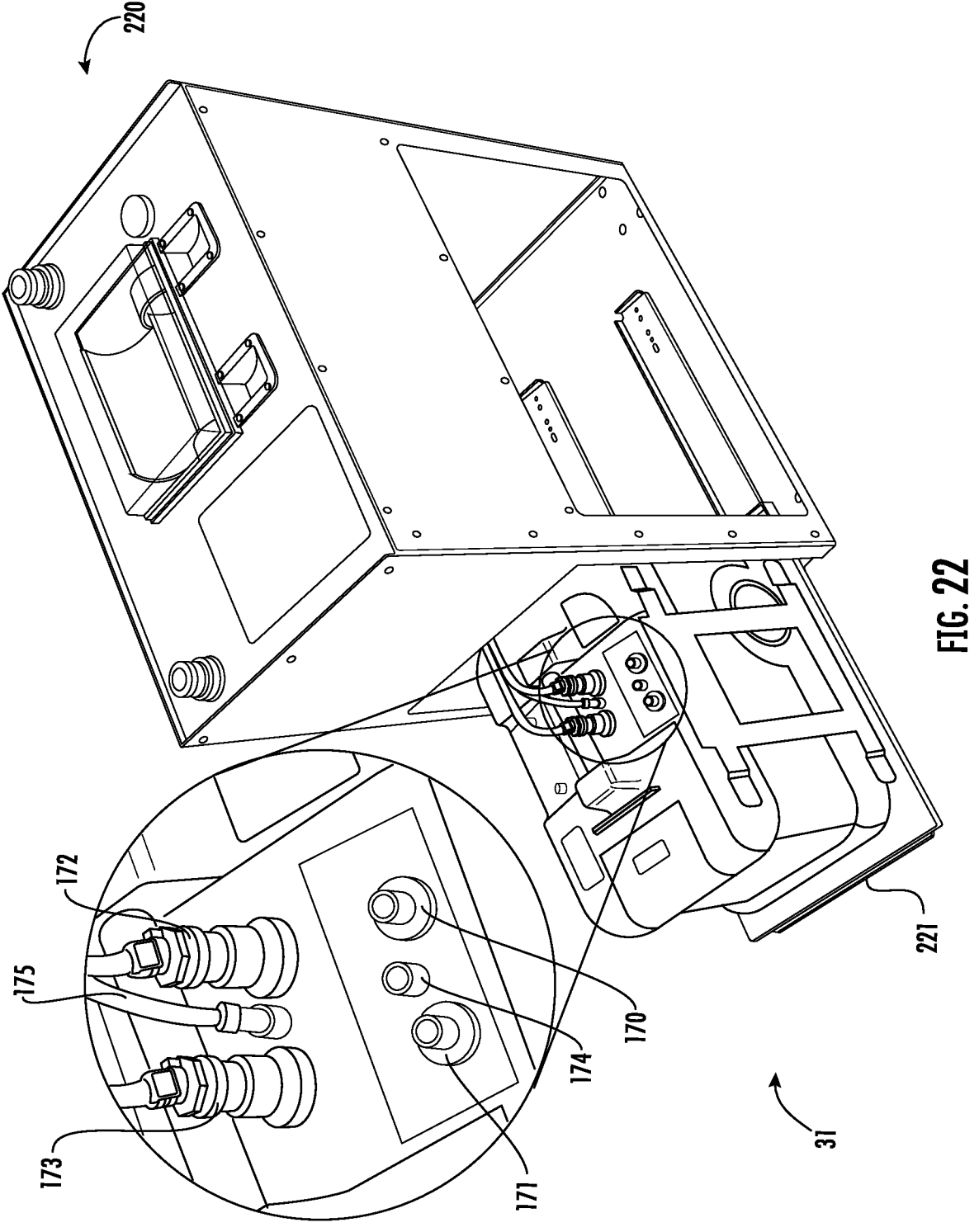
FIG. 22 is a perspective view of a fogging injection station accessory which may be used with the fogging device of FIG. 17.

Still another example fogging accessory is shown in FIG. 22, namely a fogging injection station 220. Examples of enclosed chambers which may be treated using the fogging injection station 220 include gnotobiotic chambers, isolators, HEPA filter caissons for clean rooms, air handlers, biological safety cabinets (BSCs), animal transfer stations, hypoxia chambers, mobile laboratories, incubators, etc., and may be used for numerous applications including life sciences, pharmaceuticals, biomedical, and healthcare, for example. The fogging device 31 and fogging injection station 220 advantageously provide for decontamination or sterilization of enclosed chambers to prevent human exposure to pathogens or other hazardous materials, as well as to provide disinfected/sterilized enclosures for medical or scientific applications, for example. Further details on fogging injection stations and their operation are set forth in U.S. Pat. Pub. No. 11,291,740 to Grinstead et al., which is also assigned to the present Applicant and is hereby incorporated herein in its entirety by reference.

As shown in the illustrated example, the fogging device 31 may be carried on a tray 221 within the fogging injection station 220, and air/fluid lines 172, 173 are used to connect the air compressor 34 and fluid reservoir 33 of the fogging device 31 to the fogging injection station 220 as discussed above. Moreover, an optional data/power cord 175 may also be connected from the fogging injection station 220 to the electrical/data port 174 on the fogging device 31. Here again, identification of the fogging injection station 220 to the fogging device 31 may be accomplished instead by a wireless connection or communications link in some embodiments. Moreover, the fogging device 31 may receive its power from the fogging injection station 220, or vice-versa. That is, one of the two may be plugged into a wall outlet, and the other can receive its power from the one plugged into the wall outlet for convenience. Control signals may be exchanged between the fogging device 31 and the fogging injection station 220 via the data cord 175 (or wirelessly, in some embodiments) for controlling operation of the fogging device 31 and fogging injection station 220. As with the other accessories, the fogging injection station 220 includes circuitry (e.g., a programmable logic controller (PLC), etc.) that identifies itself to the fogging device 31, so that the fogging device can place itself in the proper operating mode for the fogging injection station.

The operating mode of the fogging device 31 when connected to the fogging injection station 220 via a hard-wired connection (or wireless connection in some embodiments) may include similar parameters/control functions as the hand sprayer mode described above. One difference is that the default fluid flow may be less than for the hand sprayer 180 or standalone mode, e.g., 0.75 oz/minute or less. Moreover, control of when to start the different phases of the treatment cycle (e.g., saturation, dwell, etc.) may be turned over to the fogging injection station 220. Further, the display of the fogging device 31 may be changed to indicate it is in fogging injection station mode, and the indicators 184 on the fogging device 31 may optionally be disabled, for example.

Figure 23:
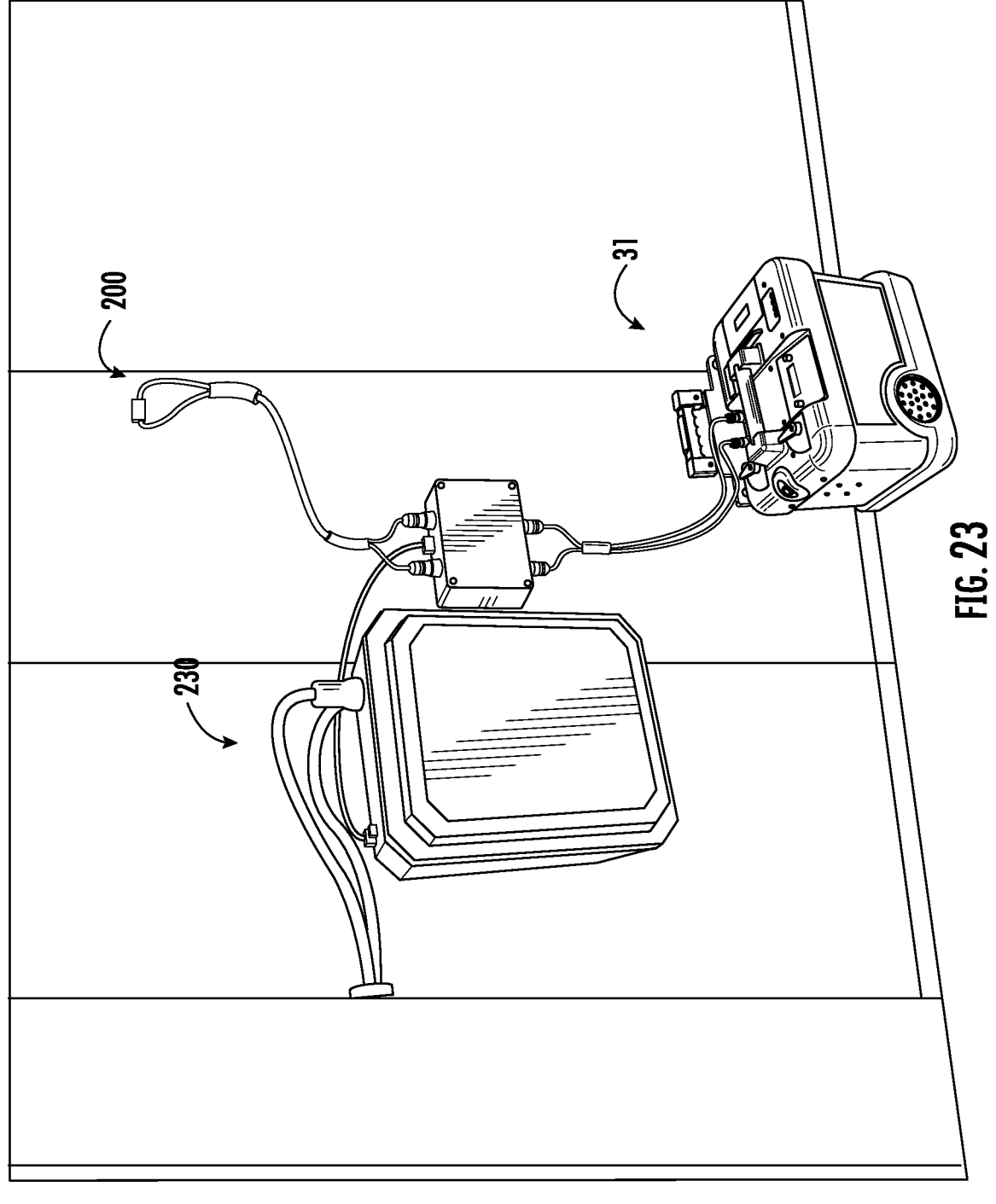
FIG. 23 is a perspective view of a facility integration module accessory which may be used with the fogging device of FIG. 17.

Another example accessory is now described with reference to FIG. 23. More particularly, this accessory is a facility integration module 230, which not only allows for the injection of atomized fluid into a room or enclosed area in a facility, but also for interaction with various systems or devices within the facility to aid in the treatment cycle. In the illustrated example, the facility integration module 230 is connected to a decontamination chamber 231, to not only inject atomized fluid into the chamber via an applicator 200 but also to allow for operation of an electronic door lock, circulation fans, exhaust fans, lights, etc., of the chamber as appropriate during the treatment cycle in an automated fashion. In other implementations, the facilities integration module 230 may be connected to a room(s) in a facility and integrate with HVAC or other systems so that they can be turned on/off or operated appropriately during a treatment cycle. As with the other accessories, the integration module 230 includes circuitry (e.g., a PLC, etc.) that identifies itself to the fogging device 31, so that the fogging device can place itself in the proper operating mode for use with the integration module. In some embodiments, different integration modules 230 may be used for different applications, and each different type of integration module may accordingly appear as a different type of accessory to the fogging device 31 for the purpose of operating mode selection.

More particularly, integration module operating modes for the fogging device 31 may include similar parameters/functions to those for the fogging injection station 220 described above. A default fluid flow rate of 1 oz/minute may be used, but here again this may be adjusted or set by the user, if desired. Moreover, the fogging device 31 may follow a different program that controls a dehumidifier 121 (see FIG. 12) to condition the chamber 231 to a lower humidity prior to saturation or injection phase, for example. Similar to the fogging injection station 220, the integration module 230 may assume control of when to start the different portions of the treatment cycle (e.g., saturation, dwell, etc.) and notify the fogging device 31 accordingly. Indicator light 184 and display states may also be changed accordingly, as discussed above.

Another operational parameter that may change from one accessory mode to the next is compliance mode operation. For example, in some applications there may be a requirement to document all fogging operations for regulatory compliance reasons. Certain accessories may have compliance mode status associated with their respective accessory types (e.g., a particular facility integration module 230 or fogging injection station 220). When connected with such an accessory that requires compliance reporting, the operating mode of the fogging device 31 may similarly include a compliance requirement, in which an approved compliance mode device 247 (see FIG. 24), such as a data logging device (e.g., memory, printer, etc.) is required for treatment to proceed. That is, compliance mode enabled/disabled may be yet another parameter that is included in the different operating modes for the various fogging accessories.

It should be noted that the accessories described above are provided by way of example, and that other fogging accessories and operating parameters/functions may be used in different embodiments.

Figure 24:
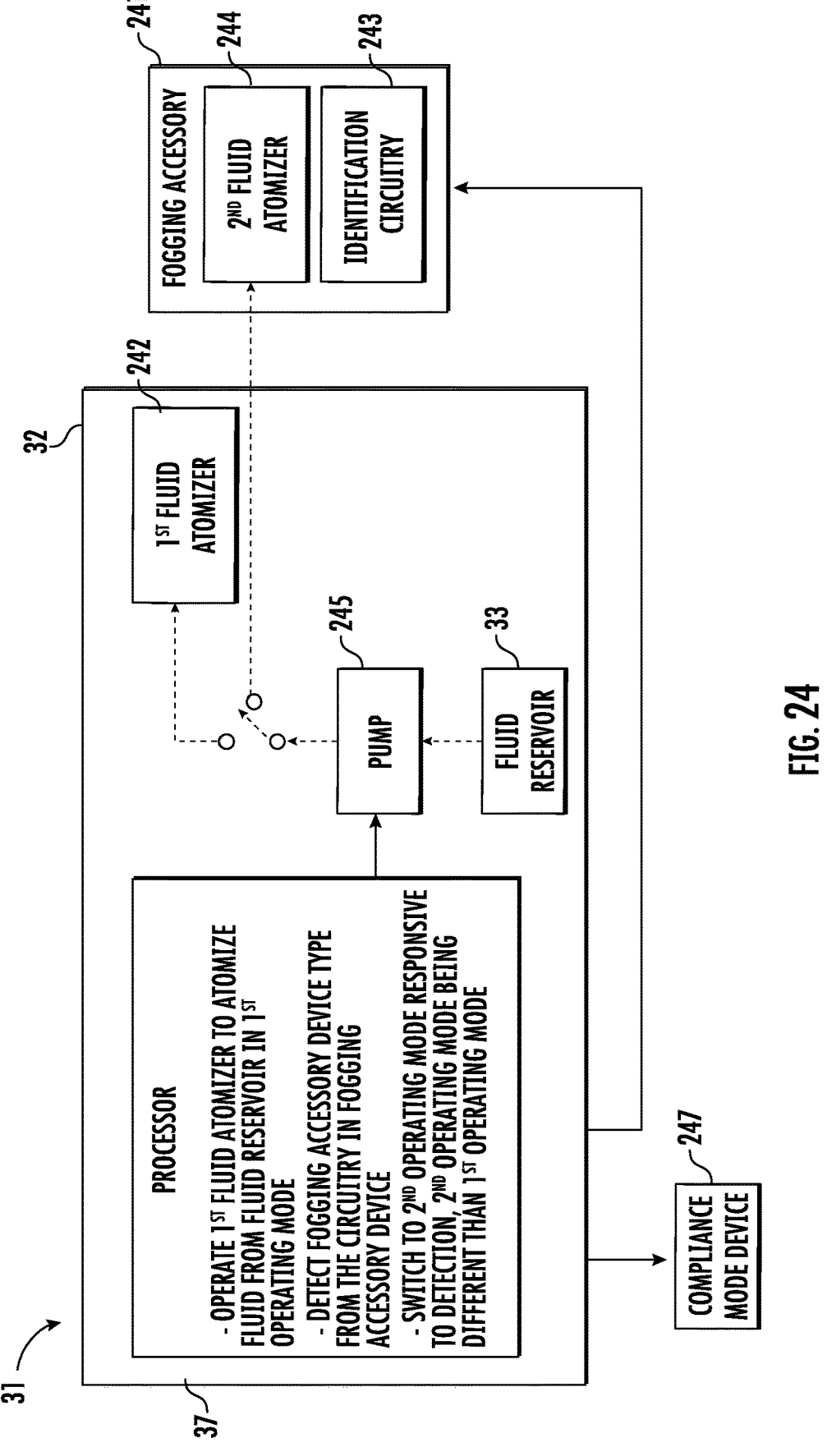
FIG. 24 is a schematic block diagram of a fogging system including a fogging device having different operational modes for different fogging accessory devices in an example implementation.
Figure 25:
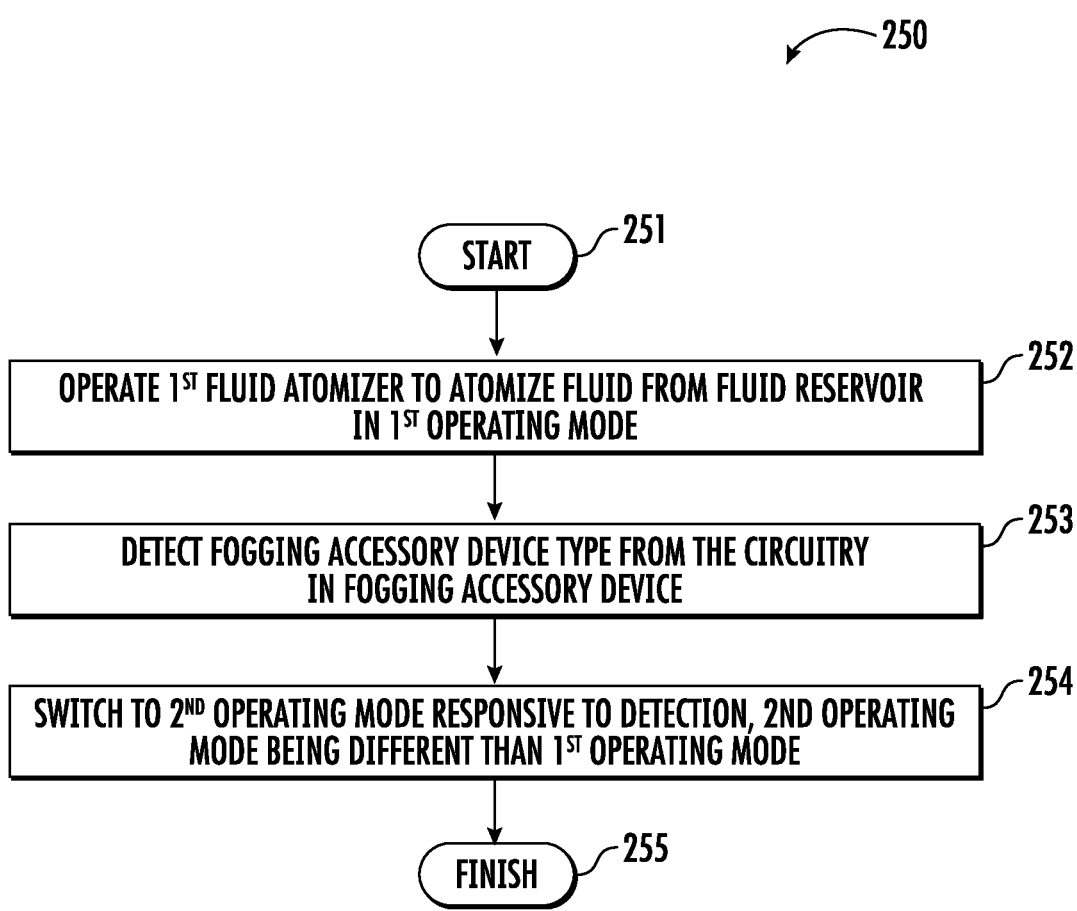
FIG. 25 is a flow diagram illustrating example operational steps which may be performed by the fogging device of FIG. 24.

Referring additionally to FIG. 24 and the flow diagram 250 of FIG. 25, an example implementation of a fogging system 240 illustratively includes a fogging device 31 and fogging accessory 241 such as those discussed further above (e.g., a hand sprayer, single/dual applicator, room integration fogging device, fogging injection station for an enclosed chamber, etc.), which in the illustrated example includes a second fluid atomizer 244. Beginning at Block 251, the fogging device 31 illustratively includes a fluid reservoir 33, a first fluid atomizer 242 (e.g., an atomizing nozzle 35) coupled to the fluid reservoir, and a processor 37 configured to operate the first fluid atomizer to atomize fluid from the fluid reservoir in a first operating mode, at Block 252.

The system 240 further illustratively includes one of a plurality of different fogging accessories 241 removably attachable to the fogging device 31 and including circuitry 243 configured to identify the fogging accessory device type associated with the fogging accessory (e.g., hand sprayer, single/dual applicator, room integration fogging device, fogging injection station, etc.), and a second fluid atomizer (e.g., an atomizing nozzle 135 or 235) configured to atomize fluid from the fluid reservoir 33 when the fogging accessory 241 is attached to the fogging device 31. The processor 37 is configured to detect the fogging accessory device type from the circuitry 243 (e.g., via a wired or wireless link), at Block 253, and switch to a second operating mode responsive to the detection, at Block 254, as discussed further above. The method of FIG. 25 illustratively concludes at Block 255.

Again, the second operating mode is different than the first operating mode, and may be different for different types of fogging accessories as well. As noted above, when the fogging device 31 includes a pump 245 coupled to the fluid reservoir 33, the processor 37 may be configured to initially operate the pump 245 in the second operating mode for priming certain types of fogging accessories 241, but not in the first operating mode, for example. In another example implementation, the fogging device 31 may be further configured to operate the pump 245 to dispense fluid from the fluid reservoir differently (e.g., change the fluid flow rate) during the first and second operating modes and for different fogging accessories 241 as well, as also discussed further above. Another example which may be different between the first and second operating modes is whether a compliance mode device 247 has to be present in order for the accessory 241 to operate, as discussed further above. It should be noted that in FIG. 24, dashed arrows indicate fluid flow paths, while solid arrows indicate data/control signal paths.

Many modifications and other embodiments will come to the mind of one skilled in the art having the benefit of the teachings presented in the foregoing descriptions and the associated drawings. Therefore, it is understood that the foregoing is not to be limited to the example embodiments, and that modifications and other embodiments are intended to be included within the scope of the appended claims.

That which is claimed is:

1. A fogging system comprising:
a fogging device comprising a fluid reservoir, a first fluid atomizer coupled to the fluid reservoir, and a processor configured to operate the first fluid atomizer to atomize fluid from the fluid reservoir in a first operating mode; and
at least one fogging accessory removably attachable to the fogging device and comprising circuitry configured to identify a fogging accessory device type associated with the at least one fogging accessory, and a second fluid atomizer configured to atomize fluid from the fluid reservoir when the at least one fogging accessory is attached to the fogging device;

wherein the processor is configured to detect the fogging accessory device type from the circuitry and switch to a second operating mode responsive to the detection, the second operating mode being different than the first operating mode.

2. The fogging system of claim 1 wherein the at least one fogging accessory comprises a plurality of different fogging accessories having different respective fogging accessory device types; and wherein the second operating mode comprises a plurality of different accessory operating modes each for a respective fogging accessory device type.

3. The fogging system of claim 1 wherein the at least one fogging accessory comprises a room integration fogging device.

4. The fogging system of claim 1 wherein the at least one fogging accessory comprises a hand sprayer.

5. The fogging system of claim 1 wherein the at least one fogging accessory comprises a fogging injection station for an enclosed chamber.

6. The fogging system of claim 1 wherein the fogging device further comprises a pump coupled to the fluid reservoir; and wherein the processor is configured to operate the pump to prime the at least one fogging accessory in the second operating mode.

7. The fogging system of claim 1 wherein the fogging device further comprises a pump coupled to the fluid reservoir; and wherein the processor is further configured to operate the pump to dispense fluid from the fluid reservoir differently during the first and second operating modes.

8. The fogging system of claim 1 wherein the processor is further configured to detect a compliance mode device adjacent the fogging device; and wherein the processor is configured to prohibit operation of the second fluid atomizer in the second operating mode when the compliance mode device is not detected.

9. The fogging system of claim 1 wherein the fogging device further comprises an LED indicator coupled to said processor; and wherein the processor is configured to operate the LED indicator differently in the first and second operating modes.

10. The fogging system of claim 1 wherein the fogging device further comprises a data port coupled to the processor; and wherein the processor is configured to detect the fogging accessory device type via a wired communications link between the data port and the at least one fogging accessory.

11. A fogging device comprising
a fluid reservoir;
a first fluid atomizer coupled to the fluid reservoir; and
a processor configured to
operate the first fluid atomizer to atomize fluid from the fluid reservoir in a first operating mode,
for at least one fogging accessory removably attachable to the fogging device and comprising circuitry configured to identify a fogging accessory device type associated with the at least one fogging accessory and a second fluid atomizer configured to atomize fluid from the fluid reservoir when the at least one fogging accessory is attached to the fogging device, detect the fogging accessory device type from the circuitry, and
switch to a second operating mode responsive to the detection, the second operating mode being different than the first operating mode.

12. The fogging device of claim 11 wherein the at least one fogging accessory comprises a plurality of different fogging accessories having different respective fogging accessory device types; and wherein the second operating mode comprises a plurality of different accessory operating modes each for a respective fogging accessory device type.

13. The fogging device of claim 11 further comprising a pump coupled to the fluid reservoir; and wherein the processor is configured to operate the pump to prime the at least one fogging accessory in the second operating mode.

14. The fogging device of claim 11 wherein the fogging device further comprises a pump coupled to the fluid reservoir; and wherein the processor is further configured to operate the pump to dispense fluid from the fluid reservoir differently during the first and second operating modes.

15. The fogging device of claim 11 wherein the processor is further configured to detect a compliance mode device adjacent the fogging device, and prohibit operation of the second fluid atomizer in the second operating mode when the compliance mode device is not detected.

16. A non-transitory computer-readable medium for a fogging device comprising a fluid reservoir, a first fluid atomizer, and a processor, the non-transitory computer-readable medium having computer-executable instructions for causing the processor to perform steps including:
operating the first fluid atomizer to atomize fluid from the fluid reservoir in a first operating mode;
for at least one fogging accessory removably attachable to the fogging device and comprising circuitry configured to identify a fogging accessory device type associated with the at least one fogging accessory and a second fluid atomizer configured to atomize fluid from the fluid reservoir when the at least one fogging accessory is attached to the fogging device, detecting the fogging accessory device type from the circuitry; and
switching to a second operating mode responsive to the detection, the second operating mode being different than the first operating mode.

17. The non-transitory computer-readable medium of claim 16 wherein the at least one fogging accessory comprises a plurality of different fogging accessories having different respective fogging accessory device types; and wherein the second operating mode comprises a plurality of different accessory operating modes each for a respective fogging accessory device type.

18. The non-transitory computer-readable medium of claim 16 wherein the fogging device further comprises a pump coupled to the fluid reservoir; and further having computer-executable instructions for causing the processor to operate the pump to prime the at least one fogging accessory in the second operating mode.

19. The non-transitory computer-readable medium of claim 16 wherein the fogging device further comprises a pump coupled to the fluid reservoir; and further having computer-executable instructions for causing the processor to operate the pump to dispense fluid from the fluid reservoir differently during the first and second operating modes.

20. The non-transitory computer-readable medium of claim 16 further having computer-executable instructions for causing the processor to detect a compliance mode device adjacent the fogging device, and prohibit operation of the second fluid atomizer in the second operating mode when the compliance mode device is not detected.

* * * * *